(12) United States Patent
Epstein et al.

(10) Patent No.: US 8,251,991 B2
(45) Date of Patent: Aug. 28, 2012

(54) ANCHORED RF ABLATION DEVICE FOR THE DESTRUCTION OF TISSUE MASSES

(75) Inventors: Gordon Epstein, Palo Alto, CA (US); Bruce Lee, Monterey, CA (US); Jeffrey M. Cohen, Pleasanton, CA (US); Adam Hagmann, Brentwood, CA (US); Richard Spero, Brentwood, CA (US)

(73) Assignee: Halt Medical Inc., Pleasanton, CA (US)

( * ) Notice: Subject to any disclaimer, the term of this patent is extended or adjusted under 35 U.S.C. 154(b) by 1230 days.

(21) Appl. No.: 11/940,294

(22) Filed: Nov. 14, 2007

(65) Prior Publication Data
US 2009/0221998 A1    Sep. 3, 2009

(51) Int. Cl.
A61B 18/18 (2006.01)
(52) U.S. Cl. .............................. 606/41; 606/33
(58) Field of Classification Search .............. 606/22–52; 607/101–102
See application file for complete search history.

(56) References Cited

U.S. PATENT DOCUMENTS

| | | |
|---|---|---|
| 35,330 A | 5/1862 | Silvester |
| 3,991,770 A | 11/1976 | LeVeen |
| 4,016,886 A | 4/1977 | Doss et al. |
| 4,074,718 A | 2/1978 | Morrison, Jr. |
| 4,080,959 A | 3/1978 | LeVeen |
| 4,095,602 A | 6/1978 | LeVeen |
| 4,119,102 A | 10/1978 | LeVeen |
| 4,140,130 A | 2/1979 | Storm, III |
| 4,154,246 A | 5/1979 | LeVeen |
| 4,230,129 A | 10/1980 | LeVeen |
| 4,285,346 A | 8/1981 | Armitage |
| 4,290,435 A | 9/1981 | Waggott |
| 4,303,636 A | 12/1981 | Gordon |
| 4,346,715 A | 8/1982 | Gammell |
| 4,375,220 A | 3/1983 | Matvias |
| 4,545,368 A | 10/1985 | Rand et al. |
| 4,565,200 A | 1/1986 | Cosman |
| 4,676,258 A | 6/1987 | Inokuchi et al. |

(Continued)

FOREIGN PATENT DOCUMENTS

DE    2124684 A1    11/1972

OTHER PUBLICATIONS

Bergamini, MD, et al., Laparoscopic radiofrequency thermal ablation: A new approach to symptomatic uterine myomas, American Journal of Obsterics and Gynecology (2005) 192, 768-73, Varese, Italy.

*Primary Examiner* — Michael Peffley
*Assistant Examiner* — Khadijeh Vahdat
(74) *Attorney, Agent, or Firm* — Handal & Morofsky LLC

(57) ABSTRACT

An anchoring member comprises a support structure and at least one anchor secured to the anchoring member. An anchor deflection member supports the anchoring member for sliding longitudinal movement in directions which result in advancement and retraction of a point on the anchor. A deflection lip is positioned relatively inwardly with respect to the guide surface. The deflection lip is positioned to outwardly deflect the point of the anchor as the anchor is advanced from a position removed from the deflection lip toward the deflection lip into contact with the deflection lip and beyond the deflection lip.

17 Claims, 22 Drawing Sheets

U.S. PATENT DOCUMENTS

| | | |
|---|---|---|
| 4,709,701 A | 12/1987 | Weber |
| 4,773,864 A | 9/1988 | Holt |
| 4,823,791 A | 4/1989 | D'Amelio et al. |
| 4,881,543 A | 11/1989 | Trembly et al. |
| 4,887,614 A | 12/1989 | Shirakami et al. |
| 4,955,884 A | 9/1990 | Grossi et al. |
| 4,962,761 A | 10/1990 | Golden |
| 5,003,991 A | 4/1991 | Takayama et al. |
| 5,007,908 A | 4/1991 | Rydell |
| 5,010,897 A | 4/1991 | LeVeen |
| 5,099,756 A | 3/1992 | Franconi et al. |
| 5,151,101 A | 9/1992 | Grossi et al. |
| 5,190,517 A | 3/1993 | Zieve et al. |
| 5,190,541 A | 3/1993 | Abele et al. |
| 5,234,004 A | 8/1993 | Hascoet et al. |
| 5,257,451 A | 11/1993 | Edwards et al. |
| 5,273,535 A | 12/1993 | Edwards et al. |
| 5,275,162 A | 1/1994 | Edwards et al. |
| 5,282,797 A | 2/1994 | Chess |
| 5,293,863 A | 3/1994 | Zhu et al. |
| 5,293,869 A | 3/1994 | Edwards et al. |
| 5,309,910 A | 5/1994 | Edwards et al. |
| 5,313,943 A | 5/1994 | Houser et al. |
| 5,314,466 A | 5/1994 | Stern et al. |
| 5,322,503 A | 6/1994 | Desai |
| 5,328,467 A | 7/1994 | Edwards et al. |
| 5,334,193 A | 8/1994 | Nardella |
| 5,342,357 A | 8/1994 | Nardella |
| 5,348,554 A | 9/1994 | Imran et al. |
| 5,363,861 A | 11/1994 | Edwards et al. |
| 5,366,490 A | 11/1994 | Edwards et al. |
| 5,368,592 A | 11/1994 | Stern et al. |
| 5,370,678 A | 12/1994 | Edwards et al. |
| 5,383,917 A | 1/1995 | Desai et al. |
| 5,385,544 A | 1/1995 | Edwards et al. |
| 5,398,683 A | 3/1995 | Edwards et al. |
| 5,403,311 A | 4/1995 | Abele et al. |
| 5,409,453 A | 4/1995 | Lundquist et al. |
| 5,423,807 A | 6/1995 | Milder |
| 5,423,808 A | 6/1995 | Edwards et al. |
| 5,423,811 A | 6/1995 | Imran et al. |
| 5,433,708 A | 7/1995 | Nichols et al. |
| 5,435,805 A | 7/1995 | Edwards et al. |
| 5,437,662 A | 8/1995 | Nardella |
| 5,456,662 A | 10/1995 | Edwards et al. |
| 5,458,596 A | 10/1995 | Lax et al. |
| 5,458,597 A | 10/1995 | Edwards et al. |
| 5,462,521 A | 10/1995 | Brucker et al. |
| 5,470,308 A | 11/1995 | Edwards et al. |
| 5,470,309 A | 11/1995 | Edwards et al. |
| 5,471,982 A | 12/1995 | Edwards et al. |
| 5,472,441 A | 12/1995 | Edwards et al. |
| 5,484,400 A | 1/1996 | Edwards et al. |
| 5,486,161 A | 1/1996 | Lax et al. |
| 5,505,730 A | 4/1996 | Edwards |
| 5,507,743 A | 4/1996 | Edwards et al. |
| 5,509,419 A | 4/1996 | Edwards et al. |
| 5,514,130 A | 5/1996 | Baker |
| 5,514,131 A | 5/1996 | Edwards et al. |
| 5,531,677 A | 7/1996 | Lundquist et al. |
| 5,536,267 A | 7/1996 | Edwards et al. |
| 5,540,655 A | 7/1996 | Edwards et al. |
| 5,542,915 A | 8/1996 | Edwards et al. |
| 5,542,916 A | 8/1996 | Hirsch et al. |
| 5,542,928 A | 8/1996 | Evans et al. |
| 5,545,161 A | 8/1996 | Imran |
| 5,545,171 A | 8/1996 | Sharkey et al. |
| 5,545,193 A | 8/1996 | Fleischman et al. |
| 5,546,267 A | 8/1996 | Frederiksen et al. |
| 5,549,108 A | 8/1996 | Edwards et al. |
| 5,549,644 A | 8/1996 | Lundquist et al. |
| 5,554,110 A | 9/1996 | Edwards et al. |
| 5,556,377 A | 9/1996 | Rosen et al. |
| 5,558,672 A | 9/1996 | Edwards et al. |
| 5,558,673 A | 9/1996 | Edwards et al. |
| 5,560,358 A | 10/1996 | Arnold et al. |
| 5,562,703 A | 10/1996 | Desai |
| 5,582,610 A | 12/1996 | Grossi et al. |
| 5,662,680 A | 9/1997 | Desai |
| 5,672,173 A | 9/1997 | Gough et al. |
| 5,672,174 A | 9/1997 | Gough et al. |
| 5,683,384 A | 11/1997 | Gough et al. |
| 5,728,143 A | 3/1998 | Gough et al. |
| 5,759,162 A | 6/1998 | Oppelt et al. |
| 5,782,827 A | 7/1998 | Gough et al. |
| 5,911,036 A | 6/1999 | Wright et al. |
| 5,935,123 A | 8/1999 | Edwards et al. |
| 5,979,453 A | 11/1999 | Savage et al. |
| 6,002,968 A | 12/1999 | Edwards |
| 6,036,689 A | 3/2000 | Tu et al. |
| 6,066,139 A | 5/2000 | Ryan et al. |
| 6,071,280 A | 6/2000 | Edwards et al. |
| 6,190,383 B1 | 2/2001 | Schmaltz et al. |
| 6,212,433 B1 | 4/2001 | Behl |
| 6,217,518 B1 | 4/2001 | Holdaway et al. |
| 6,254,601 B1 | 7/2001 | Burbank et al. |
| 6,355,033 B1 | 3/2002 | Moorman et al. |
| 6,468,273 B1 | 10/2002 | Leveen et al. |
| 6,575,967 B1 | 6/2003 | Leveen et al. |
| 6,575,969 B1 | 6/2003 | Rittman, III et al. |
| 6,837,887 B2 | 1/2005 | Woloszko et al. |
| 6,840,935 B2 | 1/2005 | Lee |
| 6,958,062 B1 * | 10/2005 | Gough et al. .................. 606/41 |
| 2001/0012956 A1 * | 8/2001 | Behl et al. ........................ 607/99 |
| 2002/0120260 A1 * | 8/2002 | Morris et al. .................. 606/41 |
| 2003/0125729 A1 | 7/2003 | Hooven et al. |
| 2003/0130711 A1 | 7/2003 | Pearson et al. |
| 2003/0199868 A1 | 10/2003 | Desai et al. |
| 2004/0215182 A1 | 10/2004 | Lee |
| 2004/0254572 A1 | 12/2004 | McIntyre et al. |
| 2005/0149013 A1 | 7/2005 | Lee |
| 2006/0189972 A1 | 8/2006 | Grossman |
| 2007/0016183 A1 * | 1/2007 | Lee et al. ....................... 606/34 |

* cited by examiner

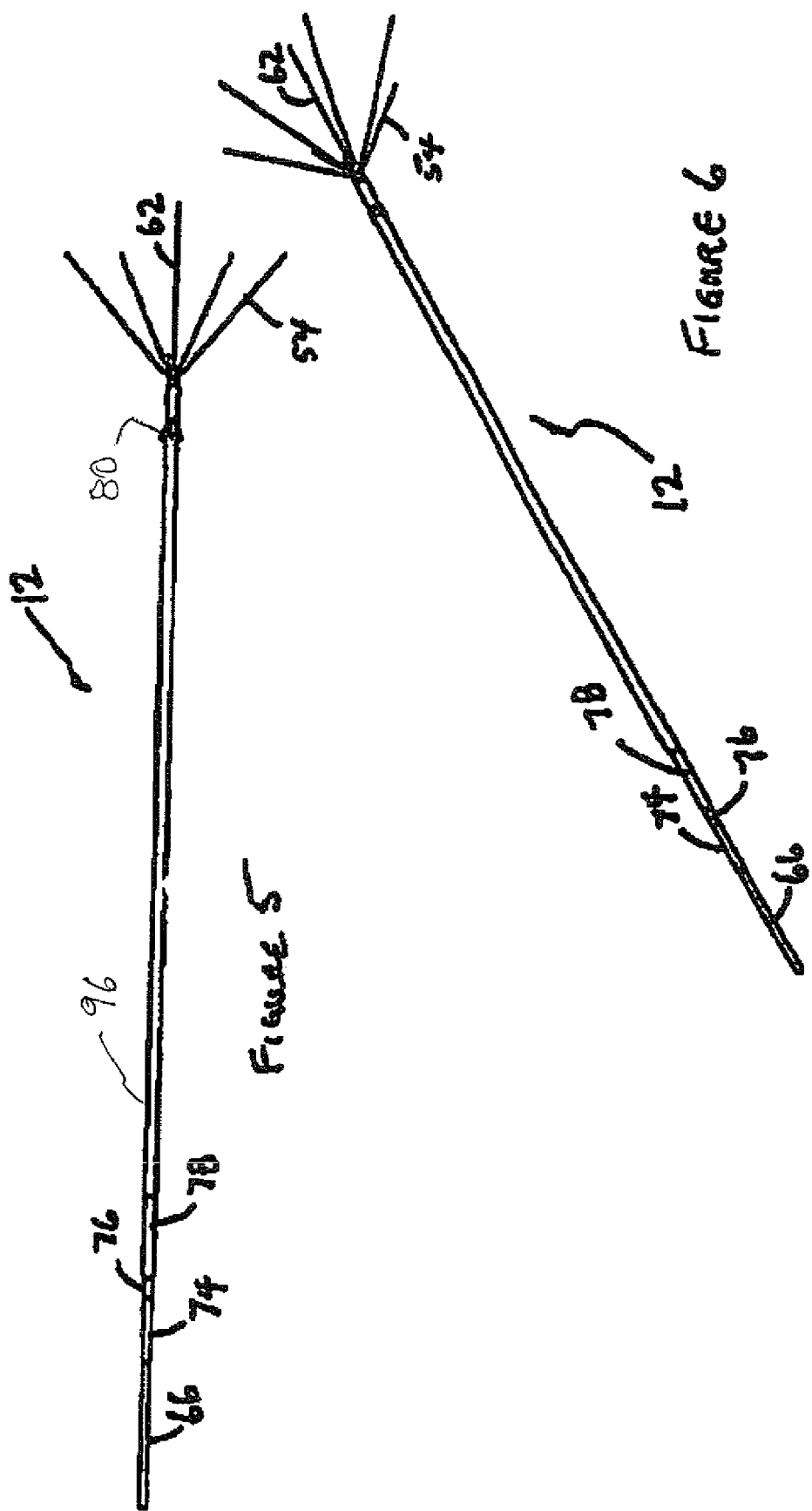

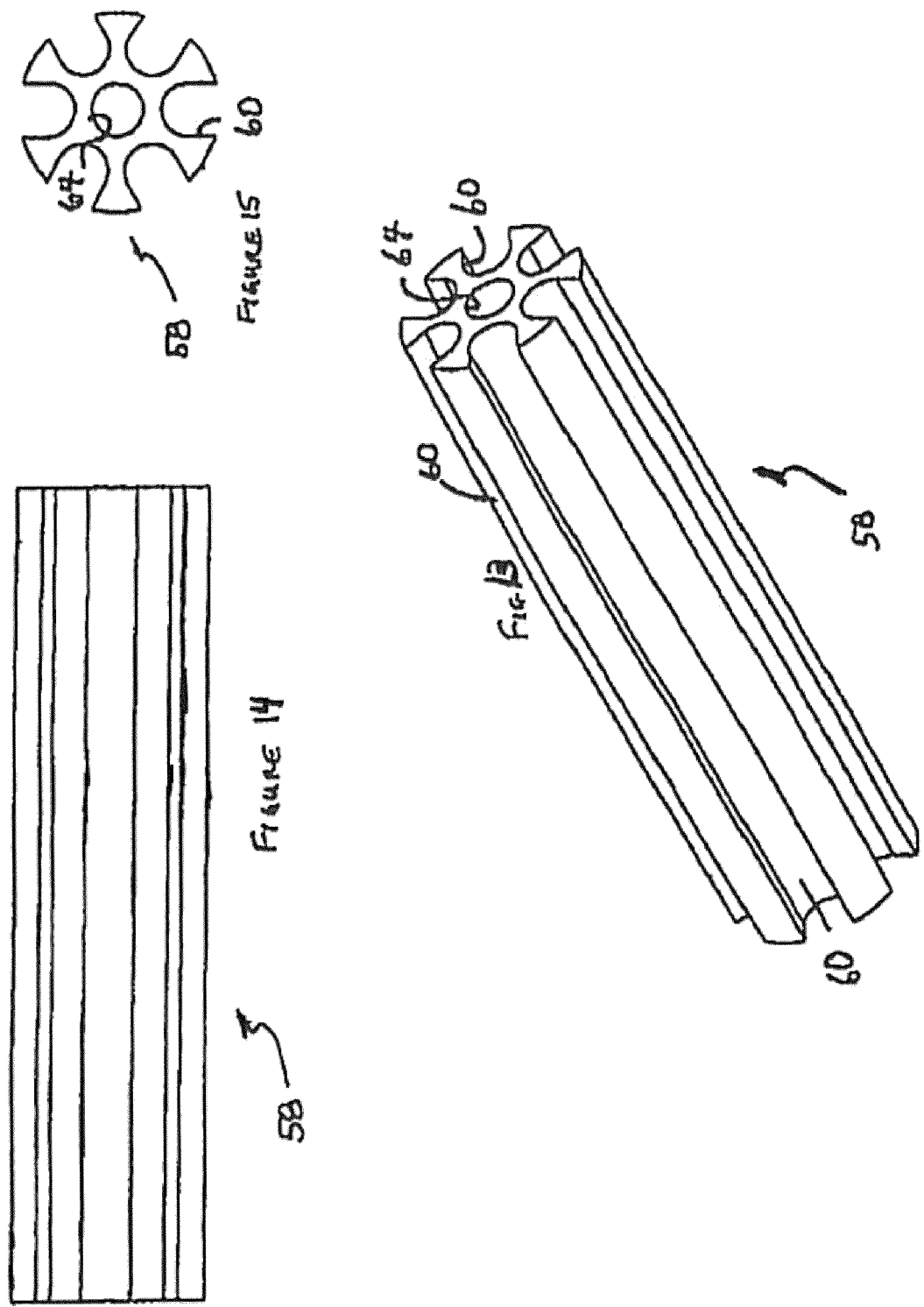

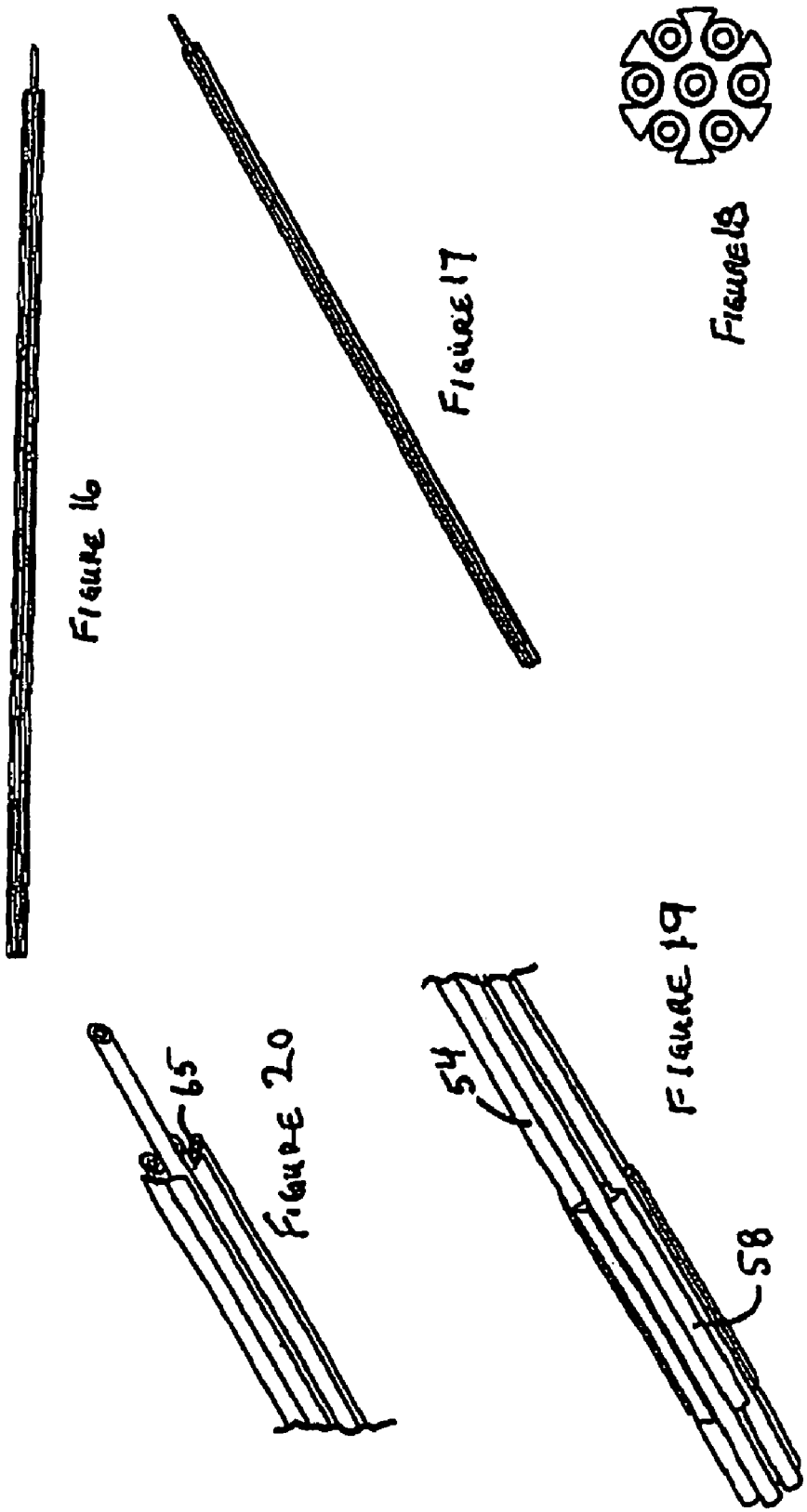

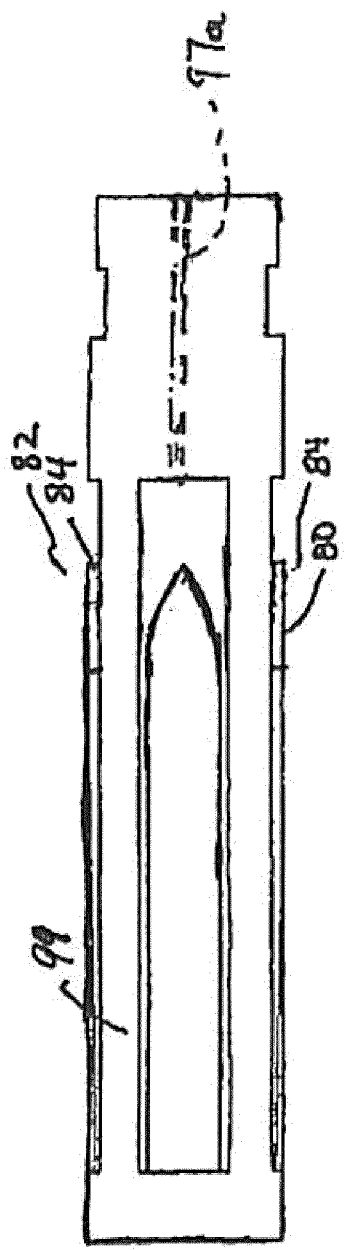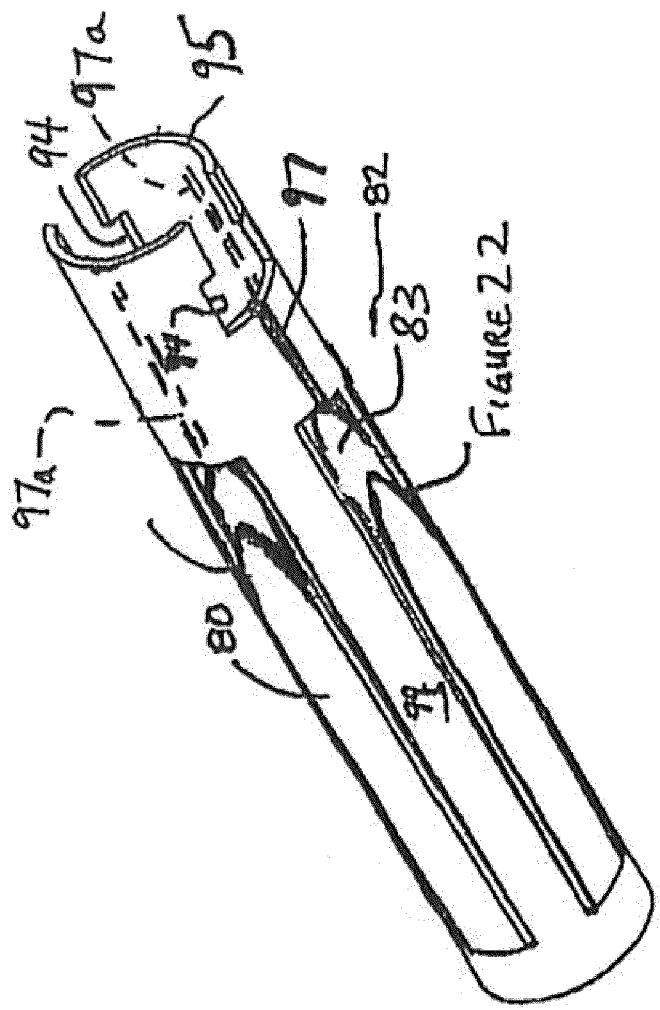

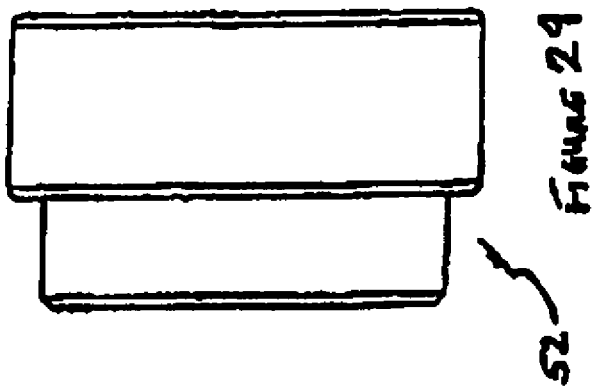
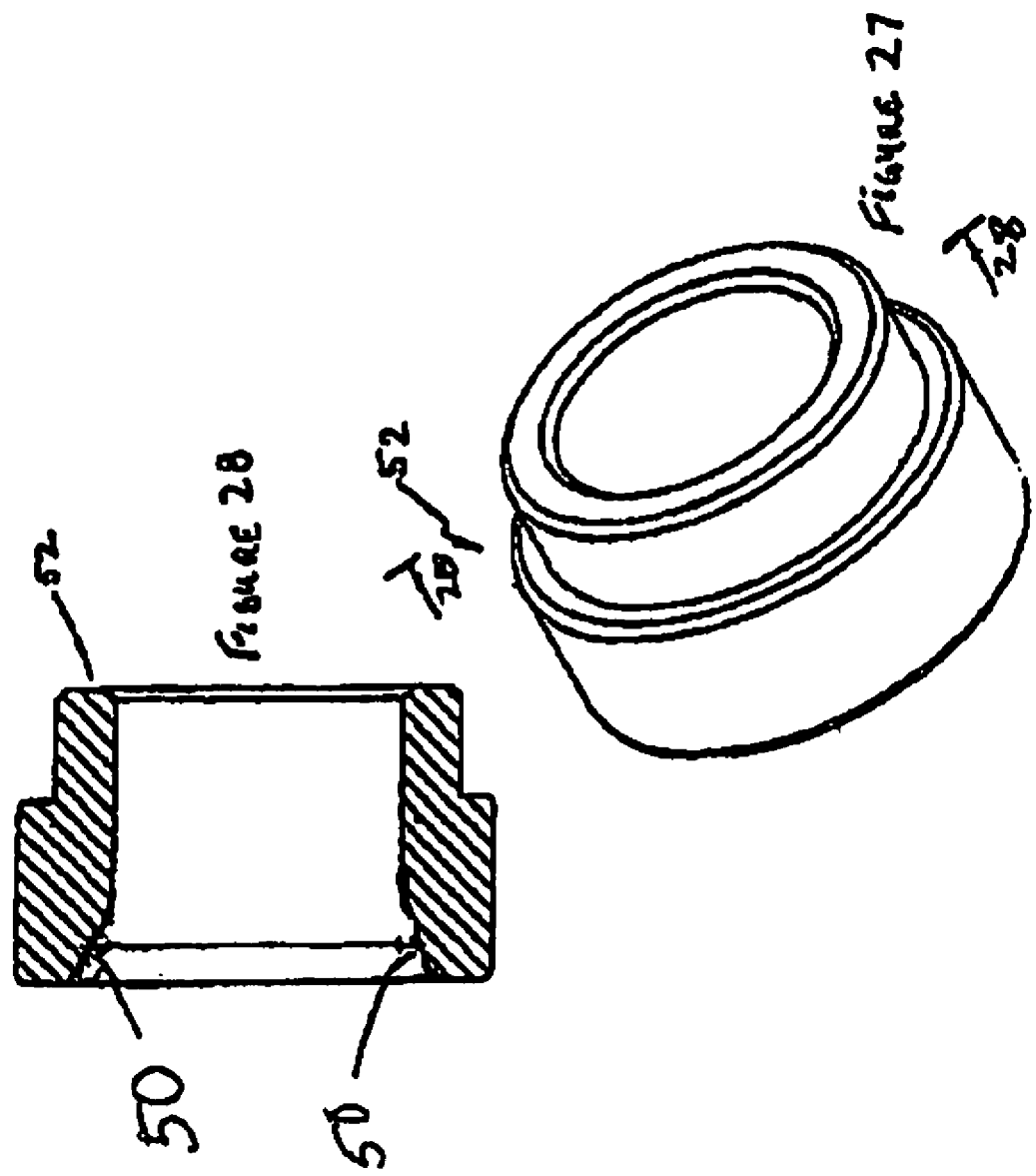

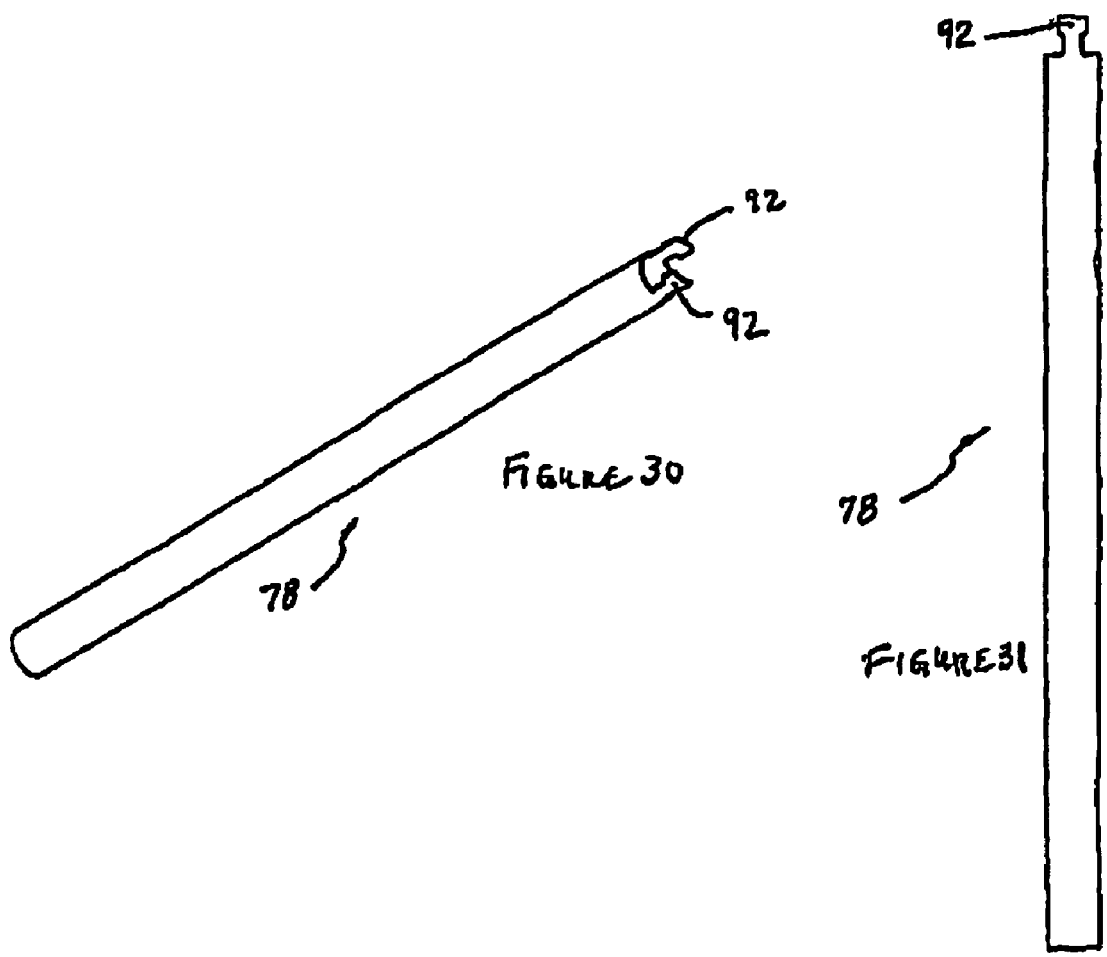

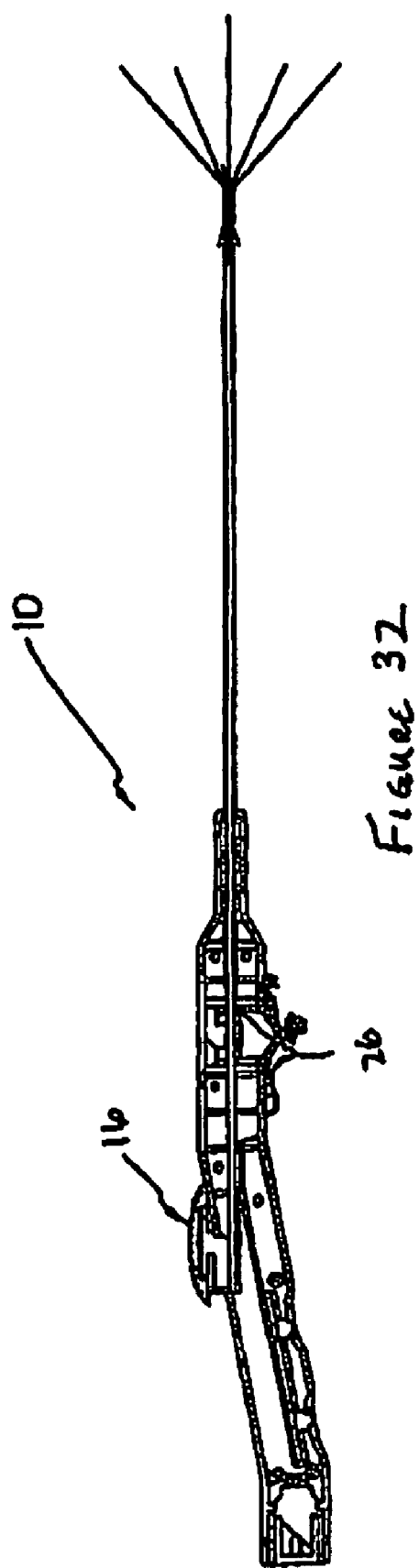

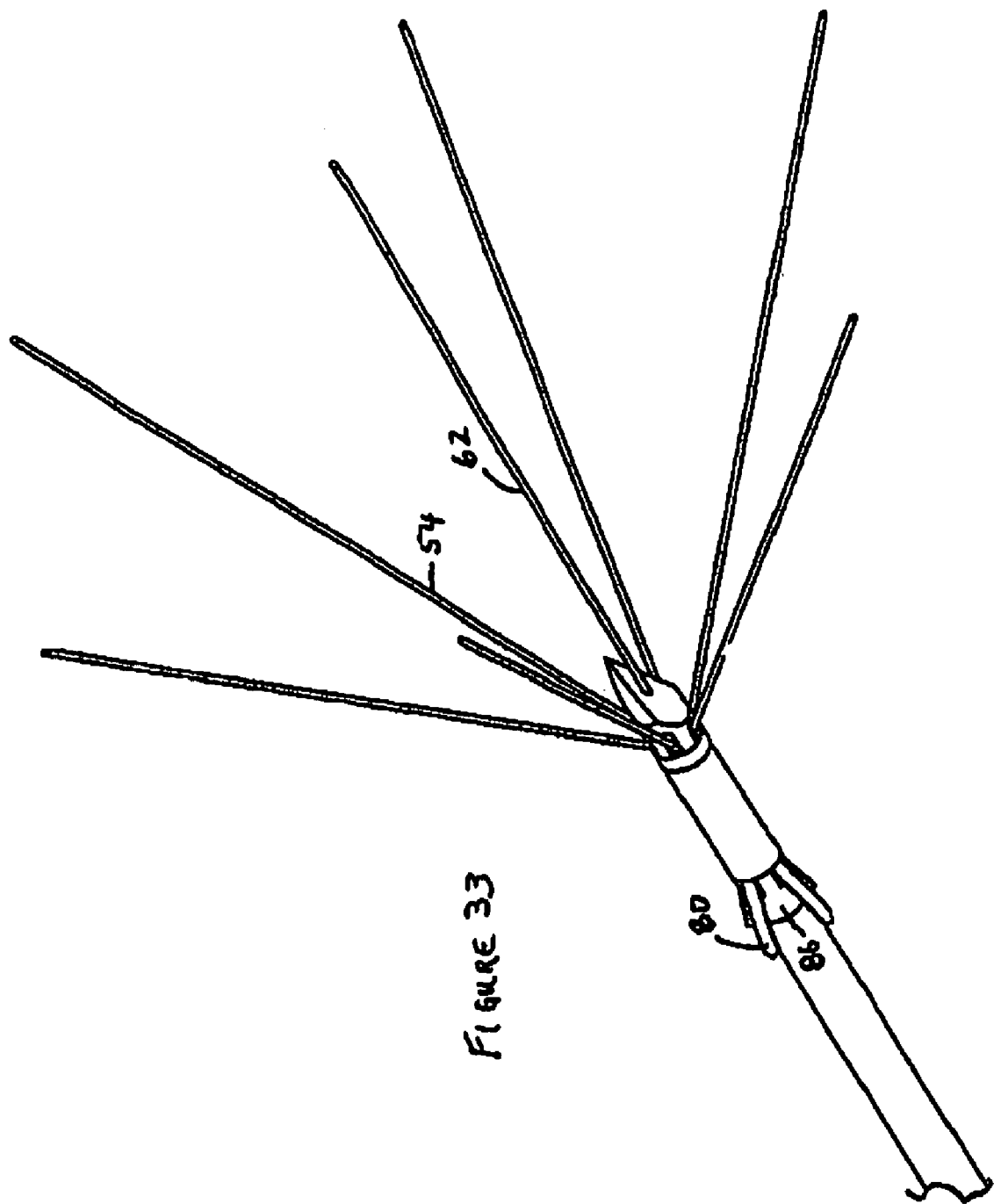

ANCHORED RF ABLATION DEVICE FOR THE DESTRUCTION OF TISSUE MASSES

CROSS REFERENCE TO RELATED APPLICATION

Not Applicable

BACKGROUND

In the United States, approximately 230,000 women have hysterectomies annually. The primary reason for performing a hysterectomy is the presence of uterine fibroids. These fibroids grow in the wall of the uterus and may range in size up to several inches across. In the United States alone, there are more than six million women with uterine fibroid symptoms who prefer to suffer, rather than endure the risks and inconveniences associated with major surgery, especially a major surgery that results in infertility. Outside of the United States, the situation is much the same, with millions of women suffering with fibroids in need of a safe alternative to hysterectomy.

Recently, another treatment option (uterine artery embolization) has been introduced. Generally, this procedure involves embolization of the arteries which feed the urine fibroid. This results in cutting off the blood supply to the fibroid and the shrinkage of the fibroid over time. However, the unacceptably high rate of complications severely limits its appeal to patients.

Myomectomy, generally involves the surgical removal of the fibroid through the use of classical surgical procedures, and is another treatment option. However, due to its high rate of complications and long recovery time, this option is also not very appealing to patients. Typical complications involve risk of infection, relatively severe post-surgical pain, damage to the uterus and other risks normally associated with such types of surgery. Moreover, such damage may be relatively subtle and may only come to light when the uterus begins to swell in pregnancy and ruptures at a weak point created during the surgery, resulting in loss of the fetus.

Still another alternative to treat the discomfort associated with uterine fibroids is the removal of the endometrium which lines the uterus. However this procedure results in infertility.

In an attempt to address these issues, an RF ablation probe of the type used to treat tumors in the human liver by hyperthermia has been successfully demonstrated to substantially shrink or eliminate uterine fibroids.

See, for example, U.S. Pat. No. 6,840,935 issued to Lee on Jan. 11, 2005, the disclosure of which is incorporated herein by reference. In that patent a method for treating pelvic tumors, such as uterine leiomyomata, includes inserting an ablation apparatus into a pelvic region and positioning the ablation apparatus either proximate to or into a pelvic tumor. The method further includes using a laparoscope and an imaging device, such as an ultrasound machine, to confirm the location of the pelvic tumor and placement of the ablation apparatus. An ablation apparatus with multiple needles or deployable arms that are inserted into the pelvic tumor is disclosed. The method involves delivering electromagnetic energy or other energy through the ablation apparatus to the pelvic tumor to induce hyperthermia and ablate the tumor.

The particular device disclosed for ablating the tumor in U.S. Pat. No. 6,840,935 is of the type disclosed in U.S. Pat. No. 5,728,143, issued to Gough et al. on Mar. 17, 1998. Generally, that device comprises a plurality of resilient springy RF ablation antennae, or stylets, which are preformed with a curved configuration which they assume after exiting a sharp trocar-tipped catheter. The tip of the catheter is deployed in uterine fibroid tissue to be destroyed. The stylets are then deployed into the tissue to be destroyed. Generally, as the antennae exit the trocar tip, they pierce the tissue of the uterine fibroid along curved paths which are defined by the preformed springy shape of the stylet. The deployed stylets with their respective preformed shapes and the positions within which they are deployed thus define the ablation volume. Various shape volumes may be defined by varying the configuration of the curves which are preformed into the different springy stylets convey given trocar-pointed catheter. Such devices are manufactured by Rita Medical Systems of Mountain View, Calif. The hallmark of such devices is that the stylets assume their pre-formed configuration as they emerge from the trocar tip.

Another approach is illustrated by copending U.S. patent application No. 11/173,928, entitled Radio Frequency Ablation Device for the Destruction of Tissue Masses filed on Jul. 1, 2005, the disclosure of which is incorporated by reference and copending U.S. patent application Ser. No. 11/429,921, entitled Anchored RF Ablation Device for the Destruction of Tissue Masses filed on May 8, 2006, the disclosure of which is incorporated by reference. The devices in both of these applications have in common the feature of deflecting the stylet and causing it to follow a path which is ideally substantially straight (or at least a substantially straighter path than that followed by the stylets in the Rita Medical device) as it advances through tissue to be ablated.

SUMMARY OF THE INVENTION

In accordance with the invention, a highly reliable anchoring mechanism for incorporation into the ablation systems is provided. The same is achieved through the use of a multi-layer anchor mandrel featuring inner surface support structures positioned at a plurality of radial distances. Guiding structure at a first radial position is positioned radially at a relatively close position to the axis of the anchor mandrel compared to the anchor. More particularly, the guiding structure comprises a deflection surface with a leading lip positioned closer to the axis of the mandrel as compared to the point of the anchor. The anchor mandrel is disposed around an anchor member. The anchor member is supported by relatively radially outwardly disposed inner surfaces of the anchor member. This allows the anchor member to be made from a tubular member (for example a circular cylindrical member) comprising anchors and support structure, and further allows the support structure to lie against the radially outwardly disposed inner surfaces of the anchor member. The structure provides the advantage that regardless of the relative axial positions of the anchor member and anchor mandrel positive engagement of the points of the anchor is assured and assembly simplified and/or the likelihood of jamming minimized.

The inventive anchoring mechanism comprises an anchoring member which comprises a support structure and at least one anchor secured to the anchoring member. An anchor deflection member is disposed generally externally to and at least partially surrounding and extending along the perimeter of the anchoring member. The anchor deflection member supports the anchoring member for sliding longitudinal movement in directions which result in advancement and retraction of a point on the anchor. The anchor deflection member defines a guide surface positioned on the inside of the anchor deflection member. The guide surface extends longitudinally, and it is configured and dimensioned to slidingly guide the cylindrical anchoring member. A deflection lip is positioned relatively inwardly with respect to the guide surface. The deflection lip is positioned to outwardly deflect the point of the anchor as the anchor is advanced from a position removed from the deflection lip toward the deflection lip into contact with the deflection lip and beyond the deflection lip.

The anchoring member may be cylindrical and circular in cross section.

The anchoring member may comprise a plurality of longitudinally extending anchors and a plurality of longitudinally extending support structures, the longitudinally extending anchors being positioned beside the longitudinally extending support structures along the perimeter of the anchoring member.

The anchor deflection member may completely encircle the anchoring member.

A second guide surface may be positioned adjacent the deflection lip and be generally oriented outwardly at an angle sufficiently shallow to result in a radius of deflection of the anchor which does not cause substantial permanent deflection of the anchor.

The anchor point may be tapered at an angle small enough to result in deflection of the point before the anchor is driven against the anchor deflection member in response to movement of the point against the deflection lip and beyond the deflection lip.

The anchors may have points adjacent one of the ends, that one of the ends defining a split ring with a gap large enough to be compressed sufficiently to allow that one of the ends to be pushed into the anchor deflection member.

The anchor deflection member may define an internal surface which is indented to receive the longitudinally extending support structures.

In accordance with the invention the inventive anchoring mechanism may be implemented in an RF ablation device of the type which comprises an elongated cannula having a proximal end and a distal end. In a typical device, the cannula defines an internal lumen within the cannula and a cannula axis. A trocar point is positioned proximate the distal end of the cannula. A conductor is contained within the cannula. The conductor has a proximal end and a distal end. The distal end of the conductor is proximate the distal end of the cannula. A plurality of ablation stylets each has a proximal end and a distal end, and each is coupled at the respective proximal end of the stylet to the distal end of the conductor. The stylets comprise a deflectable material and define a substantially straight shape. The conductor together with the stylets are mounted for axial movement within the cannula. A deflection surface is positioned between the tip of the trocar point and the proximal end of the cannula. The deflection surface is configured and positioned to deflect, in response to axial movement of the stylets in a direction from the proximate end of the cannula to the distal end of the cannula, at least one of the stylets laterally with respect to the cannula axis in different directions along paths which are substantially straight for that portion of the stylet which has exited the trocar point. These paths define an ablation volume.

The conductor may be selected from the group consisting of electrical conductors, radio frequency conductors, microwave conductors and optical conductors or light pipes.

Each of the stylets may be configured to assume a substantially straight configuration in the absence of external forces.

An ablation element further comprises a motor member or members coupled to the conductors to drive axial movement of the stylets in directions from the proximal end of the cannula to the distal end of the cannula, and from the distal end of the cannula to the proximal end of the cannula through a plurality of positions. The trocar point may be defined at the distal end of a trocar member, the trocar member having an outside surface, the cannula having an outside surface, the trocar member having a proximal end secured proximate to the distal end of the elongated cannula, and the outside surface of the cannula and the outside surface of the trocar point defining a trocar surface. The trocar member acts as a stylet mandrel to deflect the stylets, which may be electrodes, along paths which are substantially straight after the stylets exit the mandrel into the tissue to be ablated.

The deflection surface comprises a number of ramps defined proximate the proximal end of the trocar point, the distal ends of the stylets being positionable proximate to the ramps and within the trocar surface.

The conductor and the stylets are electrical conductors, and each of the stylets may be configured to assume a substantially straight configuration in the absence of external forces.

The deflection surface comprises a plurality of channels guiding the distal ends of the stylets to the ramps. The cannula may be secured to the trocar member with the outside surface of the cannula proximate to the outside surface of the trocar member.

The ablation element also comprises an anchor mounted for movement between an internal position disposed within the trocar surface and an anchoring position extending laterally from the trocar surface through points external to the lumen; and a drive member disposed within the lumen and coupled to the anchor to drive the anchor between the internal position and the anchoring position.

The anchor comprises at least two pointed members mounted for movement in directions which have vector components which extend away from the axis of the cannula and away from each other. The pointed members also preferably extend in a direction with a vector component that extends in a direction opposite to the direction in which the trocar point extends.

The conductors are driven by a drive mechanism which allows the conductors to move independently. The conductors have a length, a width and a thickness, the width being greater than the thickness, and terminate in a point oriented to allow deflection by the deflection surface. The conductors extend in different directions when they exit the deflection surface and extend to a variable extent.

The conductors are driven by a drive circuit which varies the amount of energy supplied to the stylets and/or the length of the stylets and/or the length of the time during which power is supplied to the stylets and/or the angular orientation of the ablation element (through the variation of ramp deflection angle.

The parameters of stylet length, stylet power, stylet actuation time and/or angular orientation may be controlled by a computer in response to a computer program having an input comprising feedback information from the tissue area being operated on and/or a preset program.

The anchor is mounted for movement between an internal position disposed within the trocar surface and an anchoring position extending laterally from the trocar surface through points external of the lumen. The drive member may be disposed within the lumen and coupled to the anchor to drive the anchor between the internal position and the anchoring position. The desired motive force for advancing the stylets and/or optional anchors may be provided by a finger operated slidably mounted gripping surface which the surgeon uses to manually advance the conductor and the stylets attached to the end of the conductor. The gripping surface may be slidably mounted on a handle within which the proximal end of the trocar is mounted. The anchor comprises at least two pointed members mounted for movement in directions which have vector components which extend away from the axis or the cannula and away from each other.

As alluded to above, the front end of the inventive catheter is a trocar point defined at the distal end of a trocar member. The trocar member has an outside surface. The cannula has an outside surface, and the trocar member has a proximal end secured proximate to the distal end of the elongated cannula. The outside surface of the cannula and the outside surface of the trocar point define the trocar surface. The trocar member bears a plurality of deflection surfaces. The deflection surface comprises a number of ramps defined within the trocar member. The distal ends of the stylets are positionable proximate to the deflection surfaces and within the trocar surface.

In accordance with a particularly preferred embodiment of the invention, it is contemplated that a graphical user interface and a pair of electrical switches, for example a joystick and a pushbutton, will be used to switch between operating parameter options for the inventive catheter which are displayed on a graphical user interface (or other information conveying device such as an audio cue generator). The surgeon navigates a menu, for example, using a joystick looking at or hearing an electronically generated audio signal such as a voice, presenting various options and selects the desired option by pushing the electrical switch. In principle, this can be done on a single switch incorporating joystick and pushbutton features.

Optionally, the electrical switches which operate the system may be recessed partially or fully in order to minimize the likelihood of unintentional actuation. Additional protection may be provided by requiring two motions within a relatively short period of time in order to achieve a change in the control of the system.

In accordance with a particularly preferred version of the invention, is achieved by having a human voice present options and acknowledge instructions, which may be given to the system orally using voice recognition technology. This allows the surgeon to operate without having to look away from visual displays guiding the operation, the patient, instruments and so forth, thus removing potential losses of information. A display simultaneously displays all relevant information to provide a quicker provision of information to the surgeon.

In accordance with the invention it is contemplated that laser manufacturing techniques may be used to manufacture the anchors and perhaps the anchor deflection surfaces.

Preferably, the point of the trocar is milled to a point with three surfaces. Stylets are milled in the manner of a hypodermic needle. Stylets are oriented to cooperate with the deflection surfaces which deflect them. A cooperating low friction insulator ring, for example, made of Teflon, cooperates with the deflection surfaces to deflect hypotube electrode stylets.

The present invention contemplates the use of rearwardly deployed anchoring stylets which act as retractable barbs for maintaining the position of the trocar point during forward deployment of the radiofrequency (RF) electrode ablation stylets.

In accordance with the present invention, a stylet operating member, optionally a stylet push member, which may be a tube, is positioned on one side of a tubular compression/tension operator, for example on the inside of the compression/tension operator. Similarly, in accordance with the present invention, and anchor member operating member, optionally an anchor pull member, which may be a tube, is positioned on the other side of a tubular compression/tension operator, for example on the outside of the compression/tension operator. Such outside placement is particularly advantageous in the case where the anchoring member is of relatively wide dimension and large size.

In accordance with a preferred embodiment of the invention, the compression tension operator is secured at the proximal end to the handle of the ablation instrument and at the distal end to the anchoring member deflection surface and the hypotube electrode stylet deflection surface.

The invention contemplates a plurality of hypotube electrode stylets which are bound together as a unitary structure and advanced by a single push tube or wire.

It is also contemplated that the inventive instrument will include channels for flushing clean. In accordance with the inventive system, the frequency with which flushing should be performed is minimized through the use of a trocar front face which is substantially closed (except for a single undeflected hypotube which exits the front face of the trocar) and providing for exit of hypotubes through the cylindrical side wall of the trocar point.

In accordance with a particularly preferred embodiment of the invention, the anchor member is separate from the anchor push tube, and is connected it to by mating or other interlocking structure.

Deflection surfaces for both the hypotube stylets and anchors are selected to result in strains in the range of 2% to 8%, preferably about 4%, for example 3.5% to 4.5%, which represents a reasonable compromise between instrument longevity and a relatively large amount of deflection.

An insulation sleeve is positioned between the anchors and the hypotube stylets in order to allow separate electrical actuation and ablation with either or both of the anchors and the hypotube stylets.

The hypotube stylets contain thermocouples which are used to measure the temperature of ablated tissue, thus ensuring that the tissue will be raised to the correct temperature for a sufficient period of time to ablate tissue resulting in the creation of necrotic tissue which may be absorbed by the body.

In accordance with the preferred embodiment of the invention, hypotube stylets are deployed forwardly or distally while anchors are deployed in a proximal direction or rearwardly. Alternatively, the hypotube stylets may be deployed in a proximal direction or rearwardly, while anchors are deployed forwardly or distally.

As compared to a conventional hysterectomy, the present invention is directed to a device for the treatment of uterine fibroids and other tissue masses that meets the needs of women by conserving the uterus and reducing recovery time from 6-8 weeks to 3-10 days.

BRIEF DESCRIPTION OF THE DRAWINGS

FIG. 5 is a plan view of the catheter with seven hypotube ablation electrodes and four anchors deployed;

FIG. 6 is a perspective view of the catheter structure of FIG. 5;

FIG. 13 is a perspective view illustrating a core for holding a plurality of hypotubes;

FIG. 14 is a side plan view illustrating a core for holding a plurality of hypotubes;

FIG. 15 is a rear view illustrating a core for holding a plurality of hypotubes;

FIG. 16 is a side plan view illustrating a core holding a plurality of hypotubes;

FIG. 17 is a perspective view illustrating a core holding a plurality of hypotubes;

FIG. 18 is a rear view illustrating a core holding a plurality of hypotubes;

FIG. 19 is a perspective detailed view illustrating a core holding a plurality of hypotubes;

FIG. 20 is a perspective detailed view illustrating the tips of a plurality of hypotubes when they are being held in a core as illustrated in FIG. 19;

FIG. 21 is a side plan view illustrating the improved rearward anchoring member;

FIG. 22 is a perspective view illustrating the rearward anchoring member of FIG. 21;

FIG. 27 is a perspective view of an insulating ring for insulating the hypotube electrodes from the anchors;

FIG. 28 is a cross-sectional view of an insulating ring for insulating the hypotube electrodes from the anchors along lines 28-28 of FIG. 27;

FIG. 29 is a side view of the insulating ring for insulating the hypotube electrodes from the anchors;

FIG. 30 is a perspective view illustrating the anchor push tube;

FIG. 31 is a side plan view illustrating the anchor push tube in accordance with the present invention;

FIG. 32 is partially cross-sectional view, similar to FIG. 1 illustrating the inventive instrument with anchors and hypotubes deployed; and FIG. 33 is a detail perspective view illustrating deployment of anchors and hypotube ablation stylets.

DETAILED DESCRIPTION OF THE BEST MODE

Figure 1:
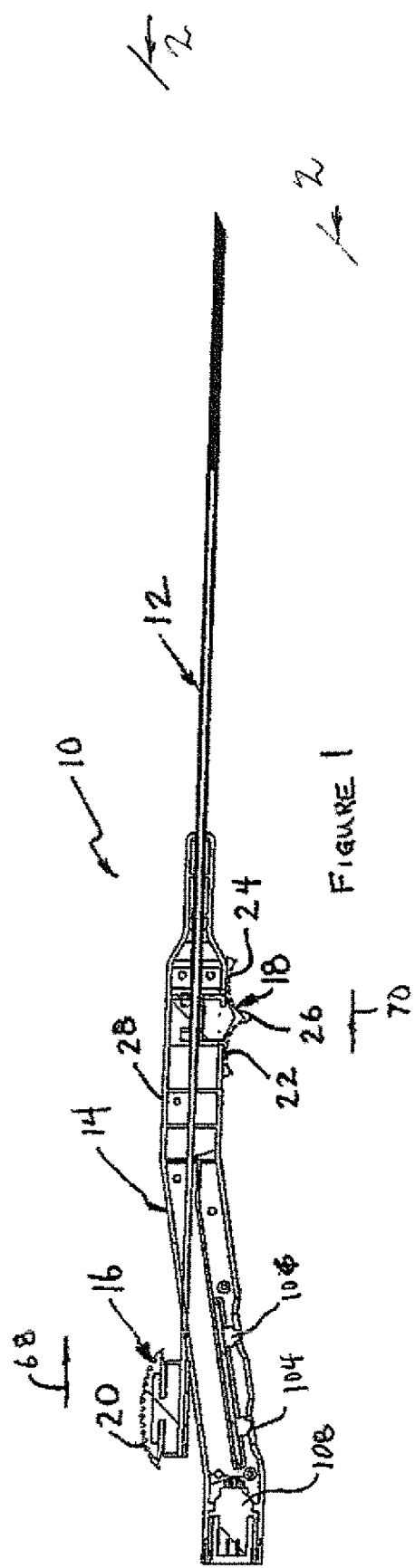
FIG. 1 is a plan view of the multiple antenna ablation device of the invention with the cover removed and partially in cross-section to illustrate its operation.

Referring to FIG. 1, an ablation instrument 10 constructed in accordance with the present invention is illustrated. Instrument 10 comprises a catheter portion 12 and a handle portion 14. Ablation instrument 10 is illustrated with one of the two mating handle halves removed and partially in cross section, in order to reveal its internal parts and workings in connection with the following description.

Figure 2:
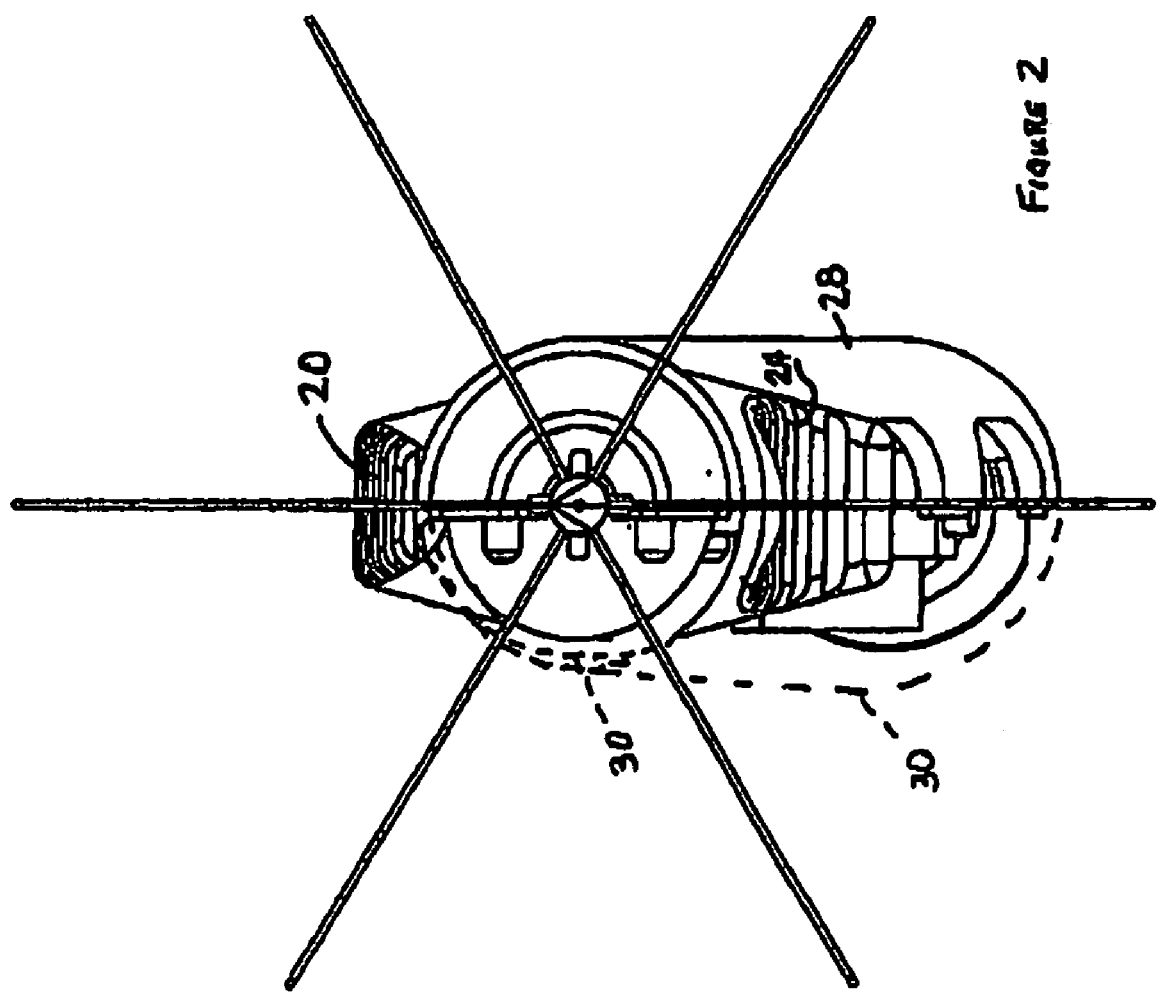
FIG. 2 is a front view of the inventive probe with anchor system of the device along lines 2-2 of FIG. 1, but illustrating the instrument after deployment of the anchor and antennae (stylets)

Referring to FIGS. 1 and 2, the inventive ablation instrument 10 is illustrated in the fully retracted position suitable for advancement of catheter portion 12 into tissue, for example, tissue to be subjected to ablation by being treated with radiofrequency energy. In this position, the catheter 12 present a simple thin smooth pointed surface well-suited to penetrate healthy tissue while doing minimal damage. At the same time, the sharpness of the point and the relatively stiff, though somewhat flexible, nature of catheter 12 enables accurate steering of the point and control of the path of penetration. In the case of the treatment of uterine fibroids, such steering is achieved largely by manipulation of the uterus coupled with advancement of the catheter 12.

Handle portion 14 includes a pair of actuators namely a stylet actuator 16 and an anchoring actuator 18. Stylet actuator 16 includes a serrated surface 20. Anchoring actuator 18 includes a pair of serrated surfaces, namely an anchor retraction surface 22 and an anchor deployment surface 24. The application of relatively great force is facilitated by a wall 26, against which the thumb or other finger of the surgeon may bear during the respective deployment and retraction phase of an operation performed using the inventive ablation instrument 10. Stylet actuator 16 and anchoring actuator 18 are supported within handle portion 14. Handle portion 14 comprises a left housing half 28 and a right housing half 30 symmetrical in shape to left housing half 28, as illustrated in FIG. 2.

Figure 3:
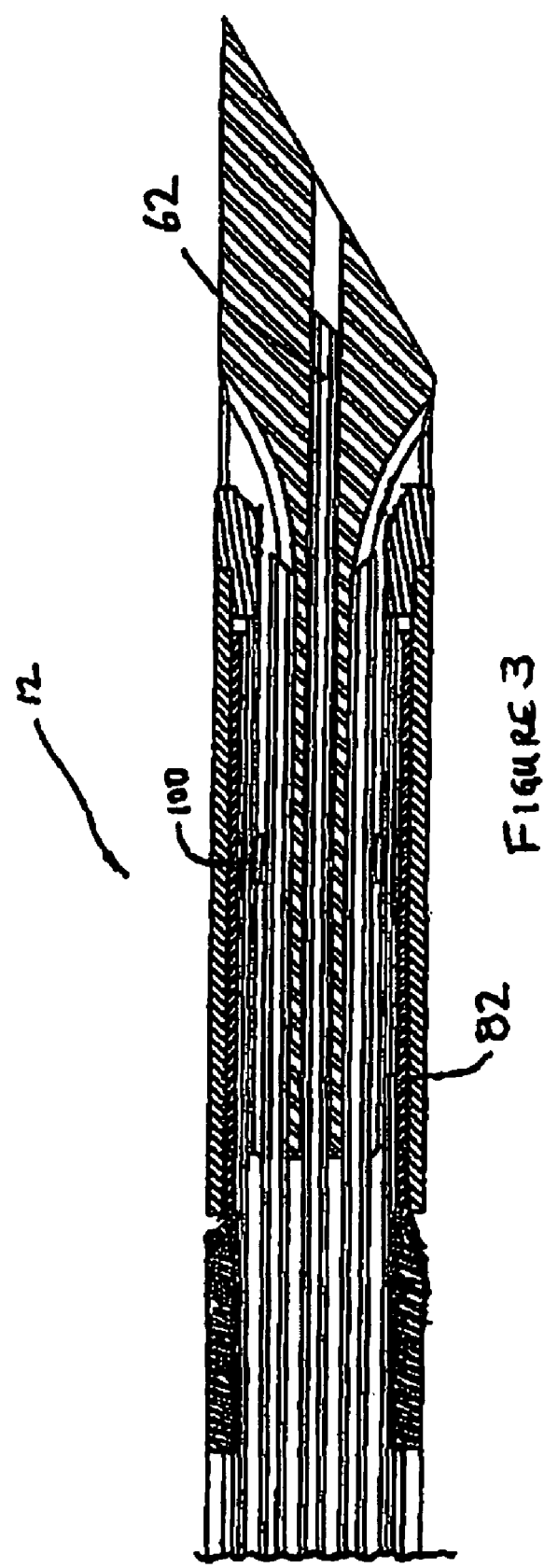
FIG. 3 is a cross-sectional view of the tip of the catheter constructed in accordance with the present invention.
Figure 4:
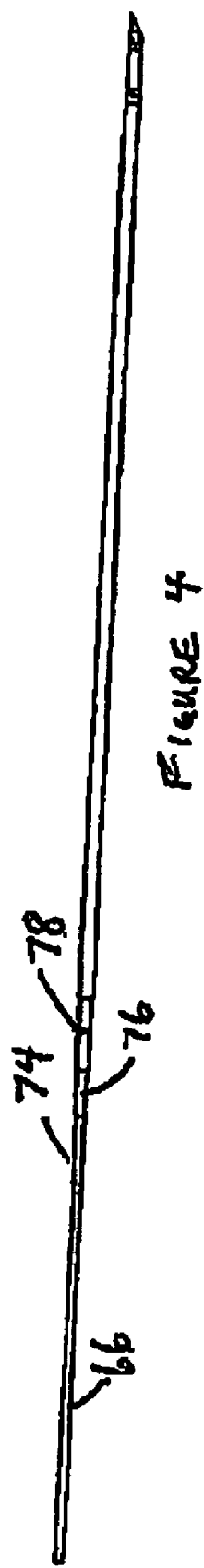
FIG. 4 is a plan view of the apparatus of the present invention with anchors and ablation hypotubes not deployed.

As illustrated in FIGS. 1, 3 and 4, the inventive ablation instrument may be configured in the undeployed state. Alternatively, as illustrated in FIGS. 2, 5, 6 and 7, the inventive ablation instrument 10 may be configured either with the anchors or the ablation stylets in a deployed state, or as illustrated in FIGS. 2, 5, 6 and 7 with anchors and stylets both fully deployed.

Figure 7:
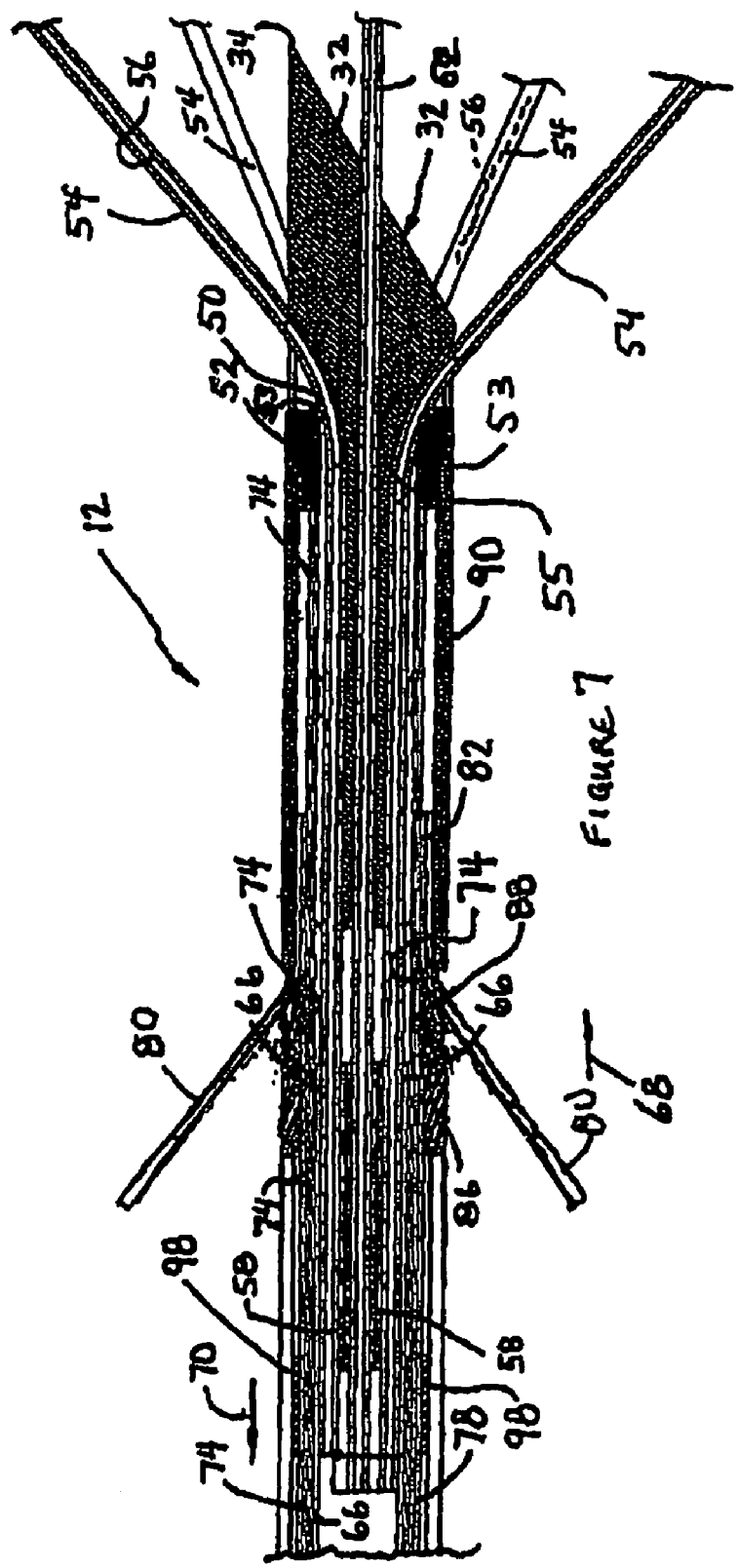
FIG. 7 is a cross-sectional view illustrating deployed hypotubes and anchors.
Figure 8:
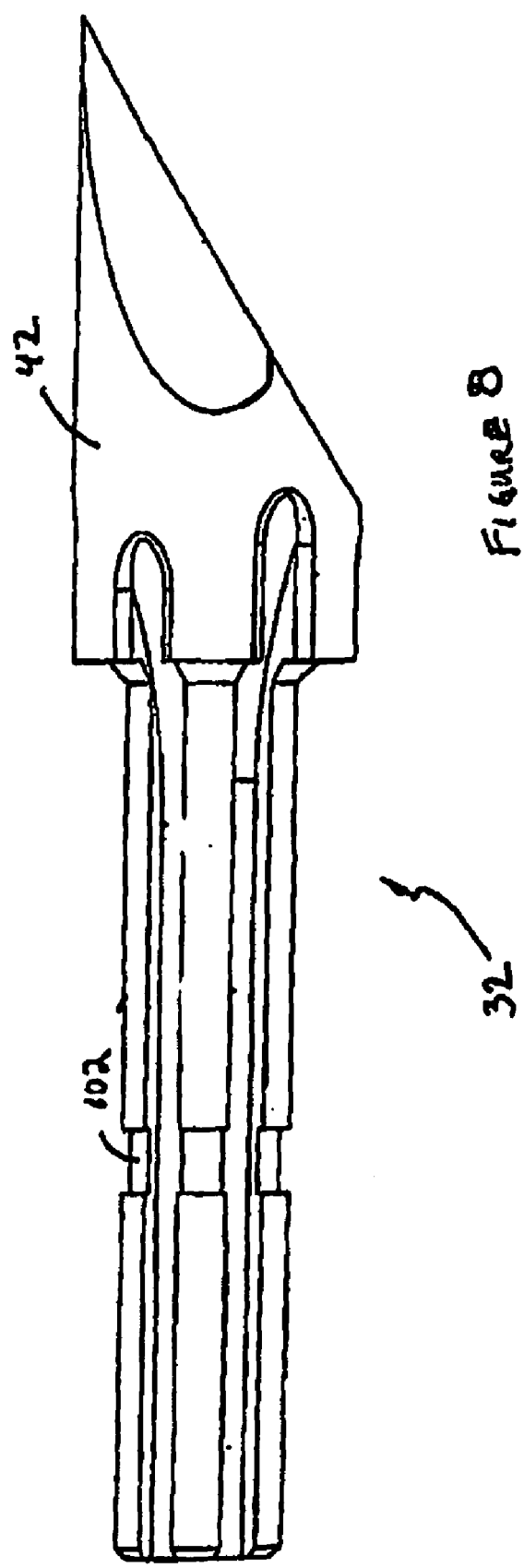
FIG. 8 is a plan view illustrating a trocar point with deflection surfaces for guiding hypotubes.

Referring to FIG. 7, ablation instrument 10 is terminated in a trocar 32, which defines a pointed tip 34. Trocar 32 also functions as an electrode mandrel to deflect the tissue ablation stylets in various directions, as appears more fully below. Trocar 32 is illustrated in FIGS. 8-12. Trocar 32 has a pointed tip 34, defined by bottom surface 36 and side surfaces 38 and 40, as illustrated most clearly in FIG. 8. Surfaces 36, 38 and 40 ground into the distal portion 42 of trocar 32. Trocar 32 also includes a central channel 44 which extends through the length of trocar 32 and is centered on the central axis of trocar 32.

Figure 9:
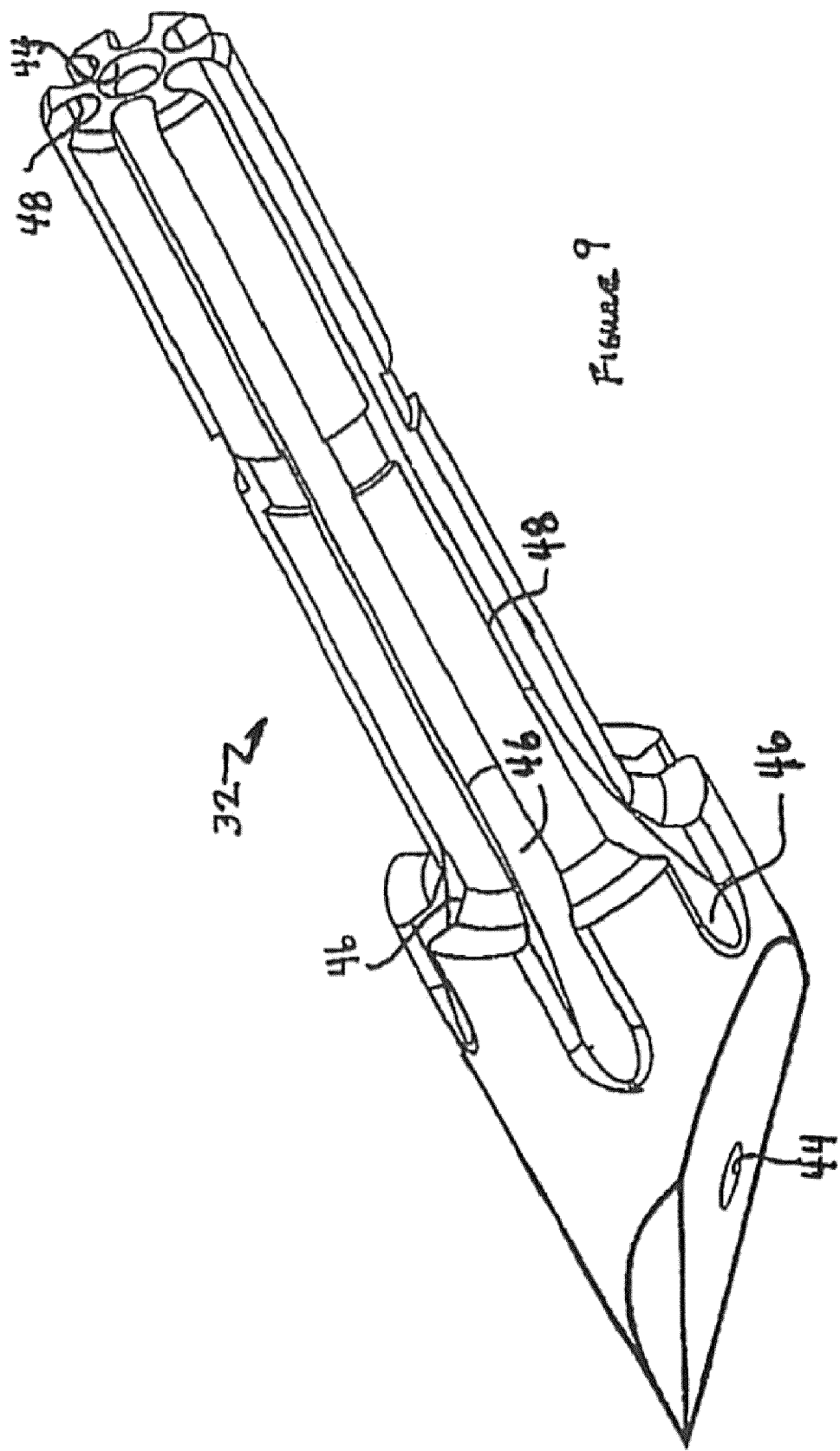
FIG. 9 is a perspective view illustrating a trocar point with deflection surfaces for guiding hypotubes.
Figure 10:
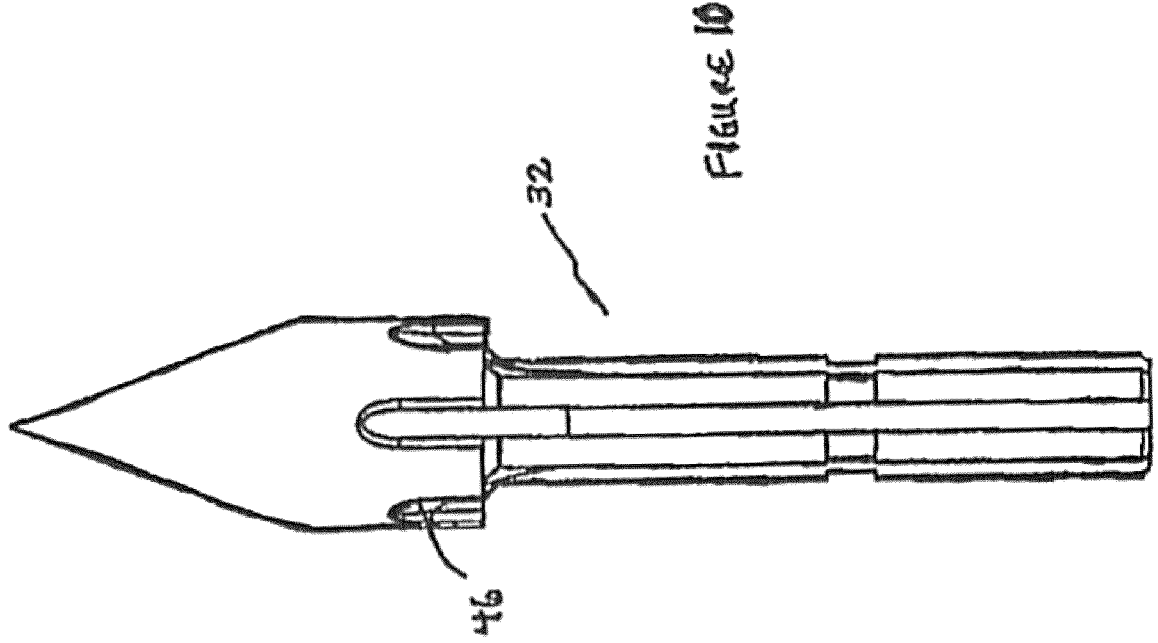
FIG. 10 is a top plan view illustrating a trocar point with deflection surfaces for guiding hypotubes.
Figure 11:
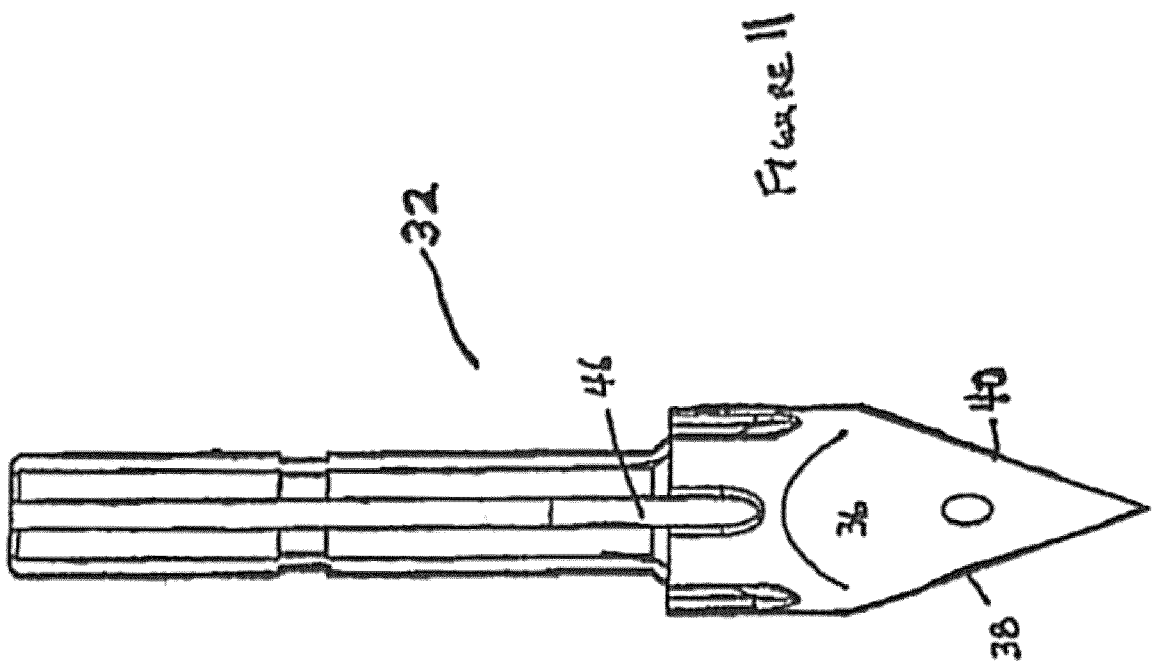
FIG. 11 is a bottom plan view illustrating a trocar point with deflection surfaces for guiding hypotubes.
Figure 12:
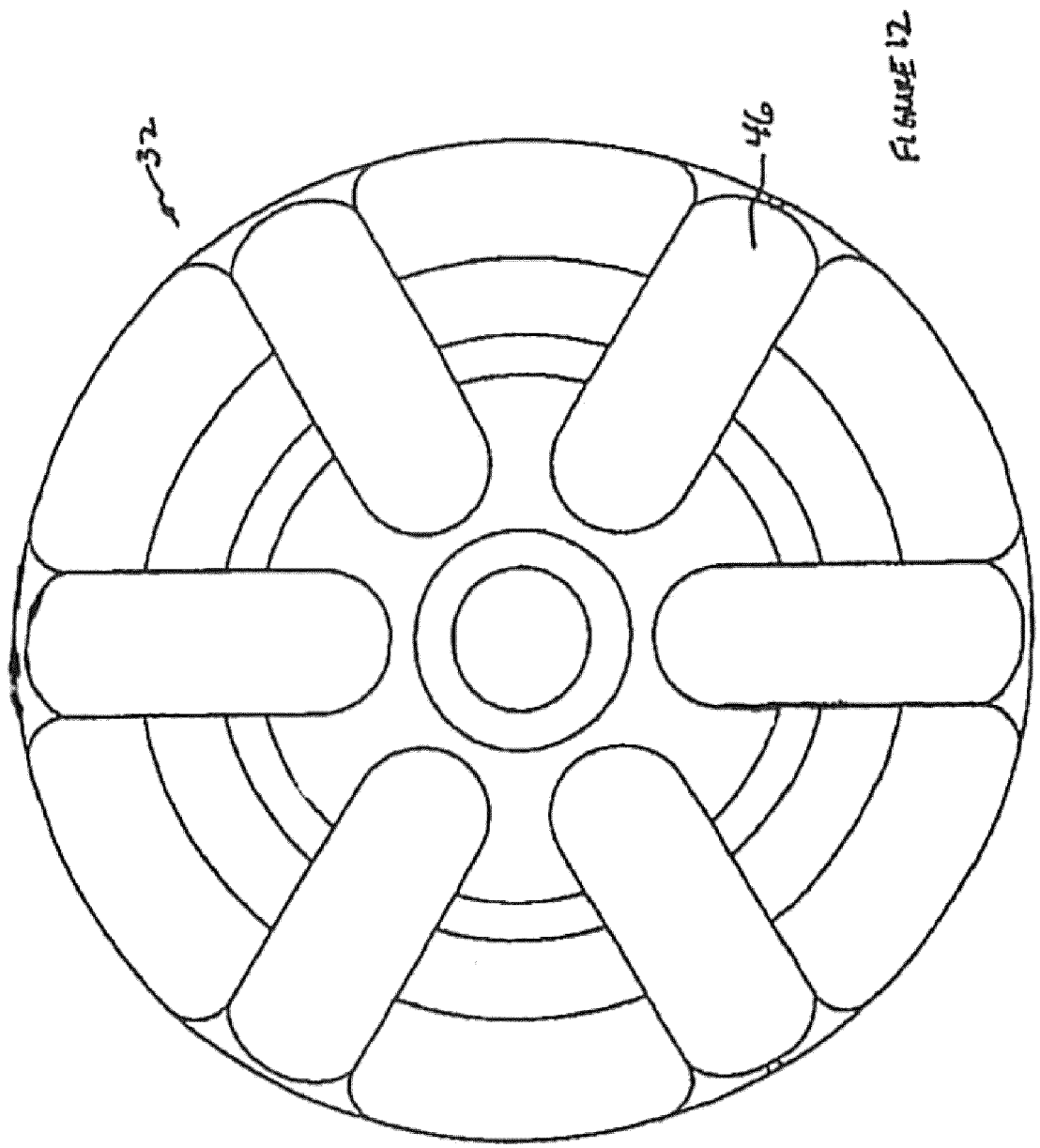
FIG. 12 is a rear view illustrating a trocar point with deflection surfaces for guiding hypotubes.

A plurality of deflection surfaces 46 are positioned at the end of longitudinal grooves 48, as illustrated in FIG. 9. These surfaces 46 are configured to gently bend the flexible hypotubes which are excited with radiofrequency energy during the ablation of uterine fibroid tissue, causing them to exit catheter 12 and follow substantially straight paths through the tissue to be ablated. During this deflection, the action of deflection surfaces 46 is complemented by the inside curved surface 50 of insulative Teflon deflector ring 52.

In accordance with a particularly preferred embodiment of the invention, the inside curved surface 50 is provided with a shape which is substantially parallel the facing portion of outside surface 53 against which stylet 54 bears. This can be seen most clearly and FIG. 28. Because a longer portion of stylet 54 is in contact with inside curved surface 50, the spring force exerted by stylet 54 tends to be distributed over a greater area, thus reducing friction as stylet 54 rights over surface 50. The difference is particularly important during that portion of time when a stylet is stationary and then begins to move. It is believed that best operation occurs when the character of stylet 54 substantially matches the curvature of surface 50. However, acceptable operation is achieved when the angle between tangents to curved surface 50 at points on the surface of the curved portion of surface 50 and facing points on the stylets (i.e. the points which define surface portion 53) which are in facing relationship to each other are 15° or less, and preferably 5° or less.

Still yet another advantage of the relatively larger radius of the curved portion of surface 50 is that stylets are bent around a radius which is relatively large, most resulting in decreasing the extent to which permanent deformation occurs, to the extent that which such permanent deformation may happen. It is noted that the extent of permanent deformation is a function of numerous factors, including the method of use, the number of times which the device is used, speed of deployment, and so forth.

When the tangents to contacting points of stylets 54 and curved surface 50 are within these angular ranges, friction is substantially reduced at surface portion 53. Accordingly, the tendency to compress surface portion 53 and expand or stretch opposite surface portion 55 is greatly reduced, Voss producing the extent to which a permanent curve may be imported to stylet 54.

This has a substantial advantage, and so far as the tendency to drive Silas 54 through tissue in a straight path as stylets 54 exit the trocar is enhanced, increasing the effectiveness with which relatively tough uterine fibroid and other tough tissues may be pierced without the need, in many cases, for preheating steps dispose between iterative advancements of the stylets into the tissue. Thus, the objective of a relatively swift performance of uterine fibroid ablation is encouraged in accordance with this aspect of the present invention.

It has also been recognized in accordance with the present invention that the material of which insulative Teflon deflector ring 52 is made will also influence the extent to which permanent deformation of stylets, in response to repeated actuation and deflection, may be avoided.

The inventive improved deflector ring 52, illustrated in FIG. 27, in addition to having a taper which is more gradual with the resulting decrease friction, is also made a material which reduces friction. Both of these factors combine to greatly reduce the tendency of the ramps in the trocar to impart a permanent bend to the stylets after repeated use.

Preferred materials for the deflector ring are materials which are not too hard. Hard materials are not desirable because of the increased friction associated with the same. Examples of materials which have been found to be too hard include polypropylene, PEEK, nylon, and PEEK with Teflon. Superior results have been achieved with PTFE (Teflon).

In accordance with an especially preferred embodiment of the invention, stylets 54 are made of a nickel titanium alloy instead of stainless steel. In this case, the configuration of deflection surfaces 46 is shaped to maximumize the deflection without over straining the nickel titanium alloy material of the stylets. More particularly, in accordance with the preferred embodiment of the invention, surfaces 46 are configured to result in a strain less than eight percent. Strains in the range of 2%-8% will work with strains in the range of about 4%, for example 3.5% to 4.5%, representing an easy to implement commercial solution. Less than 2% strain does not provide appreciable bending with today's technology. Higher performance may be obtained by maintaining a deflection angle which results in a strain of 6-7%, Configuring surface 46 to result in strains approaching 8%, for example 7.5% will maximize deflection and flexibility in design of ablation volume, but will tend to result in quicker degradation of hypotube stylets 54. However, if a particular procedure does not involve a great number of ablations, or the use of several disposable ablation catheters 10 is acceptable, such devices under certain circumstances do present advantages.

The deflection of a plurality of hypotubes 54 is illustrated in FIG. 7. Hypotubes 54 are flexible hollow tubes made of steel or nickel titanium alloy. Hypotubes 54, as well as all other steel parts of the inventive ablation device 10, are preferably, for economic and/or performance reasons, made of stainless steel or other high quality steel, except as indicated herein. The tubes define an internal volume 56 which contains a wire thermocouple, which performs the function of measuring the temperature of the ablated tissue which, over time, allows control of the ablation operation and ensures that the ablated tissue will become necrotic. In FIG. 7, the thermocouples 56 are shown in only one of the tubes for purposes of clarity of illustration.

Hypotubes 54 slidably move in longitudinal grooves 48. Hypotubes 54, which function as ablation electrodes, are mounted on a needle core 58, illustrated in FIGS. 13-15. Needle core 58 includes a plurality of longitudinal grooves 60. Each of six hypotubes 54 is mounted in its respective longitudinal groove 60 and secured in groove 60 by friction or through the use of an adhesive. A seventh hypotube 62 is mounted in a central axial bore 64. The assembly of hypotubes 54 and 62 in needle core 58 is illustrated in FIGS. 16-18. The mounting of hypotubes 54 in needle core 58 is illustrated most clearly in perspective in FIG. 19.

Hypotubes 54 may be retained in needle core 58 by any suitable means, such as a conductive cement. Alternatively, a plastic tube may be shrink-wrapped over the assembly formed by hypotubes 54 and needle core 58.

As illustrated most clearly in FIG. 20, hypotubes 54 are preferably oriented with the flat surfaces 65 of their points oriented to slidingly cooperate with deflection surfaces 46 during deployment of the hypotubes. This is done by having the pointed tips of hypotubes 54 radially displaced from the center of catheter 12, which prevents the pointed Ups of the hypotubes from digging into deflection surfaces 46.

A flexible steel electrode push tube 66 is disposed around and secured to needle core 58 with the needles mounted in it. Sliding movement of the hypotubes 54 in longitudinal grooves 48 is achieved by movement of electrode push tube 66. Movement in direction 68 causes the deployment of hypotubes 54 and 62. Movement in direction 70 causes retraction of the hypotubes.

Referring to FIGS. 5 and 7, a flexible steel electrode mandrel tube 74 is disposed around and over electrode push tube 66. Flexible steel electrode mandrel tube 74 allows electrode push tube 66 to freely slide within it. This is achieved, despite the relatively large area of the tubes, because the facing surfaces of the tubes are both smooth and because there is a small gap between their facing surfaces, thus minimizing friction. Such gaps allow provision for flushing the instrument clean with water, as is done with prior art devices. A flexible plastic tubular insulative member 76 is disposed around and over electrode mandrel tube 74.

Figure 23:
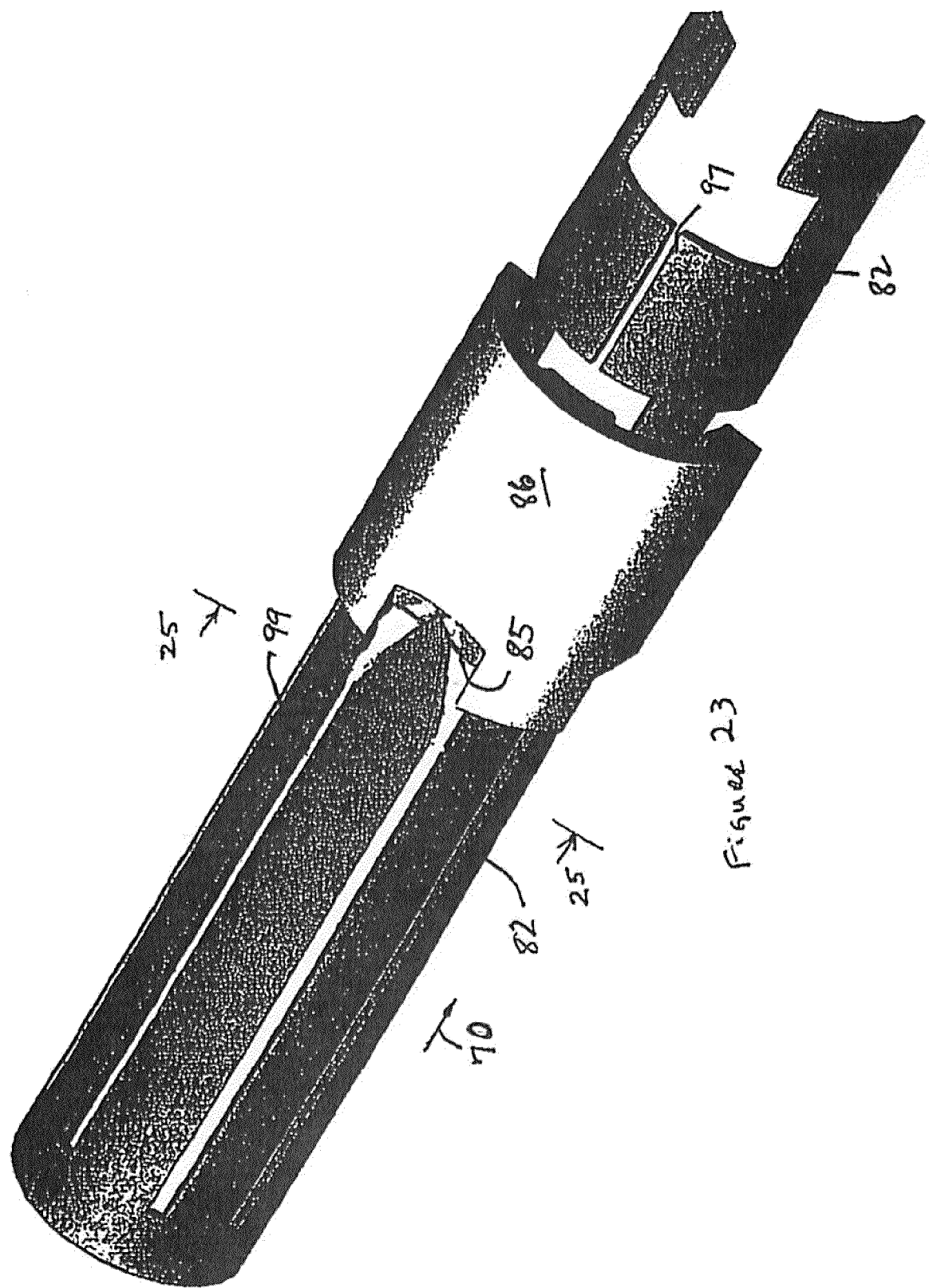
FIG. 23 is a partial perspective view illustrating the working relationship between the improved rearward anchoring member and a deflecting mandrel for deploying the rearward anchors with portions of the structure removed for purposes of clarity of illustration.

Insulative member 76 isolates electrical radiofrequency ablation energy (carried by push tube 66 for exciting hypotubes 54 and 62) from anchor push tube 78. This allows electrical ablation energy to be optionally applied to anchor push tube 78 to independently cause the anchors 80 on anchor member 82 to apply ablation energy to a different volume than that which is ablated by the electrode stylets 54 and 62. Anchor member 82 is illustrated in FIGS. 21-23. Anchors 80 are made, for example, by being cut using a laser from a steel tube to form steel anchor member 82. Each anchor 80 has a tip 84 which lies generally within the circular cylindrical surface defined by the tube from which it has been cut.

In use, the inside surface 83 of tip 84 is positioned radially outwardly with respect to the leading edges 85 of deflection surfaces 88 to facilitate deflection over anchor mandrel 86 in response to movement of anchor member 82 in the direction of arrow 70.

Anchor tips 84 come to a point forming an angle of about 60°, in accordance with the preferred embodiment. Angles ranging between 45° and 75° are preferred with angles in the range of 55° to 65° being particularly preferred. In accordance with a preferred embodiment a smooth surface extending from tips 84 to the base of the anchors is preferred.

Figure 24:
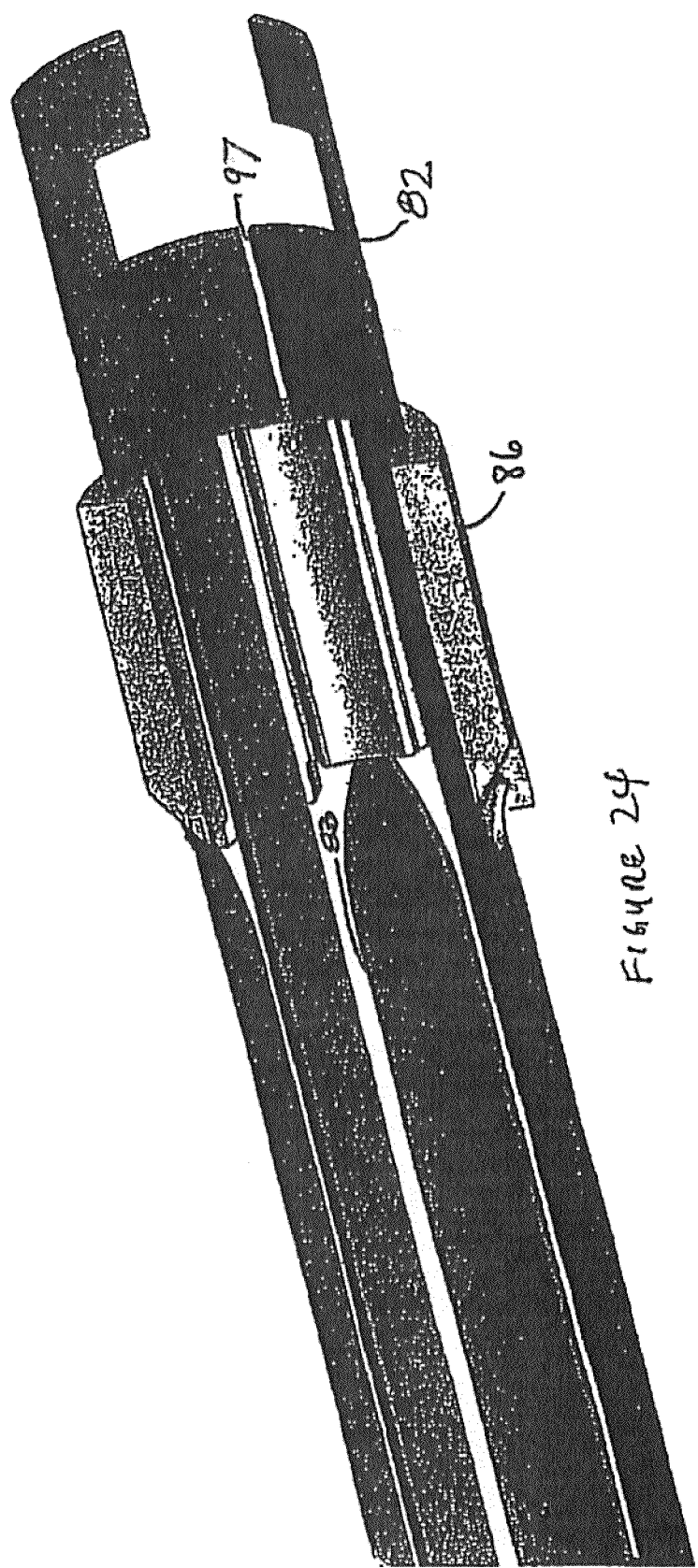
FIG. 24 is a perspective view from the rear of the partial perspective illustrated in FIG. 23.
Figure 25:
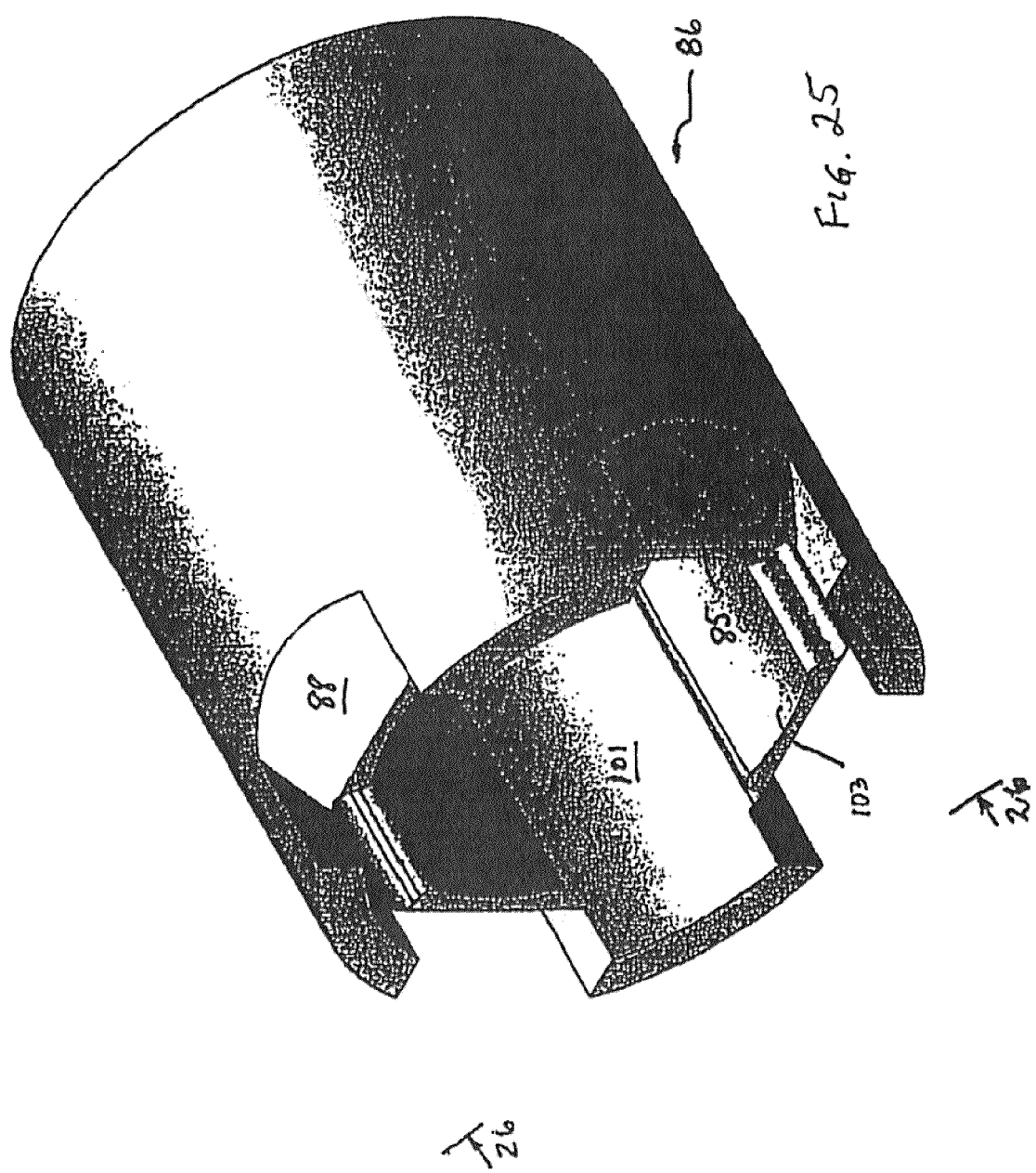
FIG. 25 it is a perspective view illustrating the anchor-deflecting mandrel.
Figure 26:
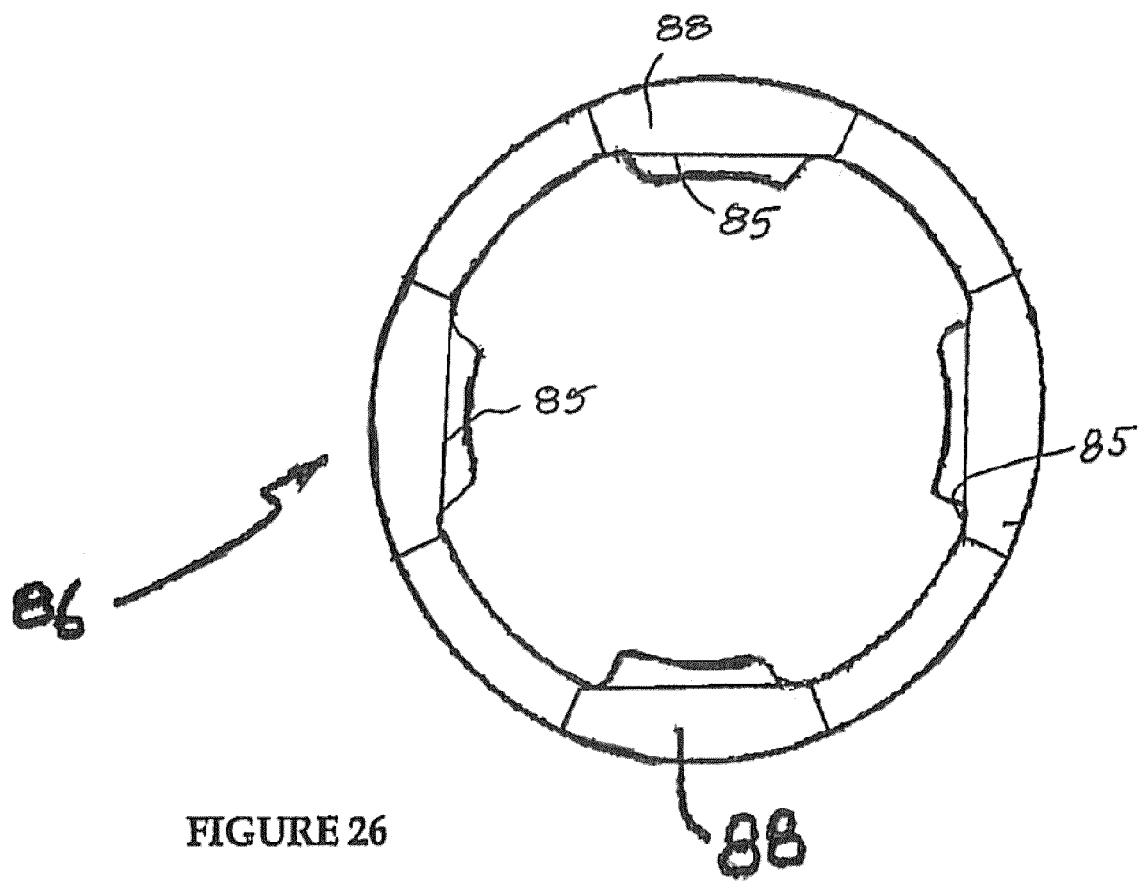
FIG. 26 is an end view illustrating an anchor deflecting mandrel member along lines 26-26 of FIG. 25.

Anchor mandrel 86 is illustrated in FIGS. 24-26. Anchor mandrel 86, which may be made of stainless steel incorporates a number of deflection surfaces 88, as illustrated most clearly in FIGS. 7 and 25. In accordance with an especially preferred embodiment of the invention, anchor member 82, and thus anchors 80, are made of a nickel titanium alloy instead of stainless steel. Nickel titanium alloy is a preferred material for both anchors 80 and stylets 54.

The configuration of deflection surfaces 88 is shaped to maximize the deflection without over-straining the nickel titanium alloy material of the anchors. The provision of anchors with points forming approximately 60° angles is particularly advantageous in this regard. In connection with this, it is noted that the anchors may have a cylindrical shape, in order to fit securely and compactly within the inventive instrument. Accordingly, the avoidance of excessive mechanical strain is additionally important, and the narrower taper assists in this regard. While points with angles in the range of about 60°, as detailed herein are preferred, angles ranging from very pointed, for example five or 10° and 60° and somewhat larger angles provide results which are superior to those achieved with, for example, 90° points.

More particularly, in accordance with the preferred embodiment of the invention, surfaces 88 are configured to result in a strain less than eight percent, even with relatively wide points, for example 90° points. With such 90° points, strains in the range of 2-8% will work with strains in the range of about 4%, for example 3.5 to 4.5%, are less rigorously 3% to 5%, representing an easy to implement commercial solution. Higher performance may be obtained by maintaining a deflection angle which results in a strain of 6-7%. Configuring surface 88 to result in strains approaching 8%, for example 7.5% will maximize deflection and flexibility in design of ablation volume, but will tend to result in quicker degradation of anchors 80. However, if a particular procedure does not involve a great number of ablations, or the use of several disposable ablation catheters 10 is acceptable, such devices under certain circumstances do present advantages.

Lower strains are achievable with 60° points and, more acute point angles.

The structure of the distal end of catheter portion 12 is completed by a steel anchor cover 90, which is supported on, surrounds and is secured to insulating ring 52 whose structure is illustrated in FIGS. 27-29. During deflection, anchors 80 pass between deflection surfaces 88 and the inside surface of steel anchor cover 90.

Anchor push tube 78, illustrated in FIGS. 30 and 31 includes a pair of keys 92 which are shaped like the letter T. Keys 92 mate with slots 94 (FIG. 22) in anchor member 82. Anchor member 82 and anchor push tube 78 thus act as a unitary member during deployment and retraction of anchors 80, in response to sliding motion of anchor member 82 and anchor push tube 78.

The insertion of end 95 of anchor member 82 into anchor mandrel 86, as illustrated in FIG. 23, is facilitated by a pair of slots 97, which allow anchor member 82 to be compressed and slid into anchor mandrel 86. Alternatively, slots 97a may be used to achieve the same purpose as illustrated in phantom lines in FIGS. 21 and 22.

Anchor member 82 generally defines a plurality of supports 99 on opposite sides of each anchor 80, as illustrated in FIGS. 21 and 22. Supports 99 ride within axially extending tracks 101 which are defined on the inside surface of anchor mandrel 86, as illustrated in FIGS. 24 and 25.

Conversely, anchor mandrel 86 defines a plurality of actually extending raised services 103 which are disposed circumferentially in between supports 99 when anchors 80 are deflected outwardly.

The structure of catheter 12 is completed by outer tube 96 which is secured to handle 14 at one end and secured to a tubular slip ring 98 which slides over anchor push tube 78.

FIG. 1 illustrates the relative positions of anchoring actuator 18, and stylet actuator 16 before deployment of anchors and stylets. This corresponds to FIG. 4.

Electrode mandrel tube 74 is secured at its proximal end to handle 14. At its distal end, electrode mandrel tube 74 is secured to trocar 32, for example by a quantity of epoxy adhesive 100 in the annular groove 102 on trocar 32, as illustrated in FIG. 3. Alternately, instead of or in addition to using an adhesive, electrode mandrel tube 74 may be crimped. Stylet actuator 16 is secured to electrode push tube 66. Thus, movement in the direction of arrow 68 in FIG. 1 causes the stylets to emerge from the end of the catheter as illustrated in FIGS. 5, 6, 7 and 32. Full deployment of ablation electrodes or stylets 54 and 62 is illustrated most clearly in FIG. 33.

Anchoring actuator 18 is secured to anchor push tube 78. At its distal end, electrode mandrel tube 74 is secured to anchor mandrel 86, for example by a quantity of epoxy adhesive. Accordingly, movement of anchoring actuator 18, in the direction of arrow 70 in FIG. 1, causes the anchors 80 to emerge from the catheter as illustrated in FIGS. 5, 6, 7 and 32. Full deployment of anchors 80 is illustrated most clearly in FIG. 33.

In accordance with the present invention it is contemplated that control of the inventive ablation device 10 will be achieved by one or two electrical switches 104 and 106. Operation of switch 106 will cause the appearance of a menu on a display, for example by axial movement of switch 106 in the manner of a joystick. Transverse movement of switch 106 causes the menu to switch between different menu items, such as controlling ablation time, controlling ablation temperature, or some other parameter. Selection of the desired value for the selected parameter is achieved by transverse motion of switch 106, causing the various values to be displayed on the display. When the desired value is seen on the screen by the surgeon, depression of switch 104 registers that value with the electronic circuit controlling ablation and causes the inventive ablation device 10 to be operated in accordance with the selected parameter.

RF ablation energy, control signals, and temperature measurement signals are coupled from the inventive ablation device 10 to a control unit/RF energy source by a connector 108. In accordance with the present invention, it is contemplated that a conventional radiofrequency energy source such as that used in conventional ablation systems would be employed in conjunction with the inventive ablation device 10.

In accordance with the present invention, cauterization radiofrequency energy may also be applied to trocar 32 during withdrawal of trocar 32 from the patient in order to control loss of blood. It is noted that the nature of the RE signal needed to achieve cautery is different from the nature of an ablation signal. Both of these signals are well defined in the art. Likewise, their generation is also well-known. However, in accordance of the present invention conventional cautery and conventional ablation signals may be used for cautery and ablation, respectively.

While the inventive device has been illustrated for use in the ablation of uterine fibroids, it is understood that this particular implementation is exemplary and that the inventive device may be employed in a wide variety of circumstances. Likewise, while an illustrative embodiment of the invention has been described, it is understood that various modifications to the structure of the disclosed device will be obvious to those of ordinary skill in the art. Such modifications are within the spirit and scope of the invention which is limited and defined only by the appended claims.

The invention claimed is:

1. An anchoring mechanism for an elongated ablation instrument having a length, a thickness smaller than said length, an instrument proximal end and an instrument distal end, said length defining an axis, said anchoring mechanism comprising:
   (a) an anchoring member, comprising:
      (i) a support structure having a configuration which extends at least partially around the axis of the ablation instrument; and
      (ii) at least one anchor, said anchor having first and second ends, said anchor being secured to said support structure proximate said first end of said anchor, said anchor being elongated in configuration and defining a tip distal to said second end configured to extend toward said instrument proximal end; and
   (b) an anchor deflection member extending along the perimeter of said anchoring member, said anchor deflection member supporting said anchoring member for sliding longitudinal movement in directions along the length of said ablation instrument which result in advancement and retraction of said point on said anchor, said anchor deflection member defining:
      (i) a guide surface positioned on said anchor deflection member, said guide surface extending longitudinally, and configured and dimensioned to slidingly guide said anchoring member; and
      (ii) a deflection lip positioned and configured to outwardly deflect said tip as said anchor is displaced
         A) from a first position removed from said deflection lip toward said deflection lip,
         B) to a second position into contact with said deflection lip, and
         C) to further displaced positions beyond said second position,
   said support structure defining at least two gaps which allow the perimeterial dimension of said support structure to be varied.

2. An ablation device comprising the anchoring mechanism as in claim 1, and further comprising:
   (c) an elongated cannula having a proximal end and a distal end, said cannula defining an internal lumen within said cannula and a cannula axis;
   (d) a plurality of ablation stylets contained within said lumen, each of said ablation stylets having a proximal end proximate the distal end of said cannula, said stylets comprising a deflectable material, said stylets being mounted for axial movement;
   (e) a leading end member having a leading end defined proximate the distal end of said cannula; and
   (f) a stylet deflection surface arrangement positioned between said leading end and said proximal end of said cannula, said stylet deflection surface arrangement being configured and positioned to deflect at least some of said stylets, in response to axial movement of said stylets in a direction from said proximate end of said cannula to said distal end of said cannula, and laterally with respect to said cannula axis in different directions along substantially straight paths, said paths defining an ablation volume, said anchor deflection member being positioned between said stylet deflection surface and the proximal end of said cannula, and said anchor deflection member being positioned relatively close to said stylet deflection surface arrangement.

3. The ablation device as in claim 2, further comprising an anchoring member drive tube mounted to slide axially within said cannula and impart an axial sliding movement to said anchoring member, and said anchoring member further defining an engagement surface which mates with said anchoring member drive tube.

4. The anchoring mechanism as in claim 1, wherein said anchoring member is cylindrical and wherein said at least one anchor comprises a plurality of longitudinally extending anchors and wherein said support structure further comprises a plurality of longitudinally extending support members, said longitudinally extending anchors being positioned adjacent said longitudinally extending support members along the perimeter of said anchoring member, and wherein said plurality of longitudinally extending support members extend between said support structure and a drive coupling portion of said anchor deflection member, said drive coupling portion of said anchor deflection member completely encircling said anchoring member.

5. The anchoring mechanism as in claim 1, wherein said tip is tapered at an angle small enough to result in deflection of said tip before the remaining portion of said anchor is driven against said anchor deflection member in response to movement of said tip against said deflection lip and beyond said deflection lip.

6. An anchoring mechanism for an elongated ablation instrument having a length, a thickness smaller than said length, an instrument proximal end and an instrument distal end, said length defining an axis, said anchoring mechanism comprising:
   (a) an anchoring member, comprising:
      (i) a support structure having a configuration which extends at least partially around the axis of the ablation instrument; and
      (ii) at least one anchor, said anchor having first and second ends, said anchor being secured to said support structure proximate said first end of said anchor, said anchor being elongated in configuration and defining a tip distal to said second end; and
   (b) an anchor deflection member extending along the perimeter of said anchoring member, said anchor deflection member supporting said anchoring member for sliding longitudinal movement in directions along the length of said ablation instrument which result in advancement and retraction of said point on said anchor, said anchor deflection member defining:
      (i) a guide surface positioned on said anchor deflection member, said guide surface extending longitudinally, and configured and dimensioned to slidingly guide said anchoring member; and (ii) a deflection lip positioned and configured to outwardly deflect said tip as said anchor is displaced
    A) from a first position removed from said deflection lip toward said deflection lip,
    B) to a second position into contact with said deflection lip, and
    C) to further displaced positions beyond said second position, said support structure defining at least one gap which allows the perimeterial dimension of said support structure to be varied, wherein said anchor deflection member is disposed generally externally to and at least partially surrounding said anchoring member, said guide surface is positioned on the inside of said anchor deflection member, and said gap allows said support structure to be compressed to a smaller perimeterial dimension and be inserted into said anchor deflection member.

7. The anchoring mechanism as in claim 6, wherein said anchoring member is cylindrical and circular in cross section.

8. The anchoring mechanism as in claim 6, wherein said anchoring member is cylindrical and wherein said at least one anchor comprises a plurality of longitudinally extending anchors and wherein said support structure further comprises a plurality of longitudinally extending support members, said longitudinally extending anchors being positioned adjacent said longitudinally extending support members along the perimeter of said anchoring member, and wherein said plurality of longitudinally extending support members extend between said support structure and a drive coupling portion of said anchor deflection member, said drive coupling portion of said anchor deflection member completely encircling said anchoring member.

9. The anchoring mechanism as in claim 6, wherein said tip is tapered at an angle small enough to result in deflection of said tip before the remaining portion of said anchor is driven against said anchor deflection member in response to movement of said tip against said deflection lip and beyond said deflection lip.

10. An anchoring mechanism for an elongated ablation instrument having a length, a thickness smaller than said length, an instrument proximal end and an instrument distal end, said length defining an axis, said anchoring mechanism comprising:
    (a) an anchoring member, comprising:
        (i) a support structure having a configuration which extends at least partially around the axis of the ablation instrument; and
        (ii) at least one anchor, said anchor having first and second ends, said anchor being secured to said support structure proximate said first end of said anchor, said anchor being elongated in configuration and defining a tip distal to said second end, said tip is configured to extend toward said instrument proximal end; and
    (b) an anchor deflection member extending along the perimeter of said anchoring member, said anchor deflection member supporting said anchoring member for sliding longitudinal movement in directions along the length of said ablation instrument which result in advancement and retraction of said tip, said anchor deflection member defining a deflection lip positioned and configured to outwardly deflect the point of said anchor as said anchor is displaced
        A) from a first position removed from said deflection lip toward said deflection lip,
        B) to a second position into contact with said deflection lip, and
        C) to further displaced positions beyond said second position,
    said support structure defining at least two gaps which allow the perimeterial dimension of said support structure to be varied, said support structure mating with a drive tube positioned to displace said support structure.

11. The anchoring mechanism as in claim 10, further comprising a second deflection surface positioned adjacent said deflection lip and generally oriented outwardly at an angle sufficiently shallow to result in a radius of deflection of said anchor by said deflection lip which does not cause substantial permanent deflection of said anchor.

12. An ablation device, comprising:
    (a) an elongated cannula having a proximal end and a distal end, said cannula defining an internal lumen within said cannula and a cannula axis;
    (b) at least one conductor contained within said lumen, said conductor having a proximal end proximate the proximal end of said cannula, and a distal end proximate the distal end of said cannula;
    (c) a plurality of ablation stylets each having a proximal end and a distal end, and each coupled at the respective proximal end of said stylet to a distal end of said at least one conductor, said stylets comprising a deflectable material, said at least one conductor and said stylets being mounted for axial movement;
    (d) a leading end member having a leading end proximate the distal end of said cannula;
    (e) a stylet deflection surface positioned between said leading end and said proximal end of said cannula, said stylet deflection surface being configured and positioned to deflect, in response to axial movement of said stylets in a direction from said proximate end of said cannula to said distal end of said cannula several of said stylets transversely with respect to said cannula axis in different directions along substantially straight paths, said paths defining an ablation volume;
    (f) an anchoring assembly positioned between said stylet deflection surface and the proximal end of said cannula, said anchoring assembly, comprising:
        (i) a support structure having a configuration which extends at least partially around the axis of the ablation instrument; and
        (ii) at least one anchor, said anchor having first and second ends, said anchor being secured to said support structure proximate said first end of said anchor, said anchor being elongated in configuration and defining a tip distal to said second end, said tip configured to extend in a direction away from said leading end, when said anchor is deflected; and
        (iii) an anchor deflection member extending along the perimeter of said anchoring assembly, said anchor deflection member being mounted for sliding longitudinal movement in directions along the length of said ablation instrument which result in advancement and retraction of said point on said anchor, said anchor deflection member defining a deflection lip positioned and configured to outwardly deflect said tip as said anchor is displaced
            A) from a first position removed from said deflection lip toward said deflection lip,
            B) to a second position into contact with said deflection lip, and
            C) to further displaced positions beyond said second position; and
    (g) a stylet deflection counter surface facing said stylet deflection surface for imparting a bend to said stylet, said support structure defining at least one gap which allows the perimeterial dimension of said support structure to be varied, and said gap allows said support structure to be compressed to a smaller perimeterial dimension to be inserted into said anchor deflection member.

13. The ablation device of claim 12, wherein said stylet deflection counter surface is made of a relatively soft plastic material.

14. The ablation device as in claim 12, wherein said tip tapers at an angle between 55 and 65°.

15. The ablation device as in claim 12, wherein said anchoring member is cylindrical and wherein said at least one anchor comprises a plurality of longitudinally extending anchors and wherein said support structure further comprises a plurality of longitudinally extending support members, said longitudinally extending anchors being positioned adjacent said longitudinally extending support members along the perimeter of said anchoring member.

16. The ablation device as in claim 12, further comprising an anchoring member drive tube mounted to slide axially within said cannula and impart an axial sliding movement to said anchoring member, and said anchoring member further defining an engagement surface which mates with said anchoring member drive tube.

17. The ablation device as in claim 12, wherein said stylet deflection counter surface is made of a relatively soft plastic material.

* * * * *